(12) United States Patent
Shingo et al.

(10) Patent No.: US 7,393,830 B2
(45) Date of Patent: *Jul. 1, 2008

(54) PROLACTIN INDUCED INCREASE IN NEURAL STEM CELL NUMBERS

(75) Inventors: Tetsuro Shingo, Okayama (JP); Samuel Weiss, Calgary (CA)

(73) Assignee: Stem Cell Therapeutics Inc., Calgary, Alberta ( * ) Notice: Subject to any disclaimer, the term of this patent is extended or adjusted under 35 U.S.C. 154(b) by 183 days.

This patent is subject to a terminal disclaimer.

(21) Appl. No.: 10/231,479

(22) Filed: Aug. 30, 2002

(65) Prior Publication Data

US 2003/0054998 A1      Mar. 20, 2003

Related U.S. Application Data

(60) Provisional application No. 60/386,404, filed on Jun. 7, 2002, provisional application No. 60/322,514, filed on Sep. 14, 2001.

(51) Int. Cl.
*A61K 36/00* (2006.01)
*A61K 36/15* (2006.01)
*A61K 36/18* (2006.01)

(52) U.S. Cl. .................. 514/12; 435/365; 435/368; 435/377; 424/198.1; 530/399

(58) Field of Classification Search ........... 435/377, 435/375, 368, 363, 365; 530/399, 300; 514/12
See application file for complete search history.

(56) References Cited

U.S. PATENT DOCUMENTS

| | | | |
|---|---|---|---|
| 4,767,628 A * | 8/1988 | Hutchinson ......... 424/426 |
| 5,023,252 A | 6/1991 | Hseih | |
| 5,128,242 A | 7/1992 | Arimura et al. | |
| 5,198,542 A | 3/1993 | Onda et al. | |
| 5,208,320 A | 5/1993 | Kitada et al. | |
| 5,231,178 A | 7/1993 | Holtz et al. | |
| 5,268,164 A | 12/1993 | Kozarich et al. | |
| 5,326,860 A | 7/1994 | Onda et al. | |
| 5,328,860 A | 7/1994 | Lee et al. | |
| 5,473,054 A | 12/1995 | Jameson et al. | |
| 5,506,107 A | 4/1996 | Cunningham et al. | |
| 5,506,206 A | 4/1996 | Kozarich et al. | |
| 5,521,069 A | 5/1996 | Onda et al. | |
| 5,527,527 A | 6/1996 | Friden | |
| 5,547,935 A | 8/1996 | Mullenbach et al. | |
| 5,559,143 A | 9/1996 | McDonald et al. | |
| 5,614,184 A | 3/1997 | Sytkowski et al. | |
| 5,623,050 A | 4/1997 | Kitada et al. | |
| 5,686,416 A | 11/1997 | Kozarich et al. | |
| 5,723,115 A | 3/1998 | Serrero | |
| 5,750,376 A | 5/1998 | Weiss et al. | |
| 5,753,506 A | 5/1998 | Johe | |
| 5,773,569 A | 6/1998 | Wrighton et al. | |
| 5,801,147 A | 9/1998 | Kitada et al. | |
| 5,833,988 A | 11/1998 | Friden | |
| 5,837,460 A | 11/1998 | Von Feldt et al. | |
| 5,851,832 A | 12/1998 | Weiss et al. | |
| 5,877,169 A | 3/1999 | Simpkins | |
| 5,885,574 A | 3/1999 | Elliott | |
| 5,955,346 A | 9/1999 | Wells et al. | |
| 5,977,307 A | 11/1999 | Friden et al. | |
| 5,980,885 A * | 11/1999 | Weiss et al. ......... 424/93.21 |
| 6,015,555 A | 1/2000 | Friden | |
| 6,017,533 A | 1/2000 | Moro et al. | |
| 6,048,971 A | 4/2000 | Sytkowski et al. | |
| 6,165,783 A | 12/2000 | Weiss et al. | |
| 6,191,106 B1 | 2/2001 | Mullenbach et al. | |
| 6,239,105 B1 | 5/2001 | Brewitt | |
| 6,242,563 B1 | 6/2001 | Dong | |
| 6,294,346 B1 | 9/2001 | Weiss et al. | |
| 6,329,508 B1 | 12/2001 | Friden | |
| 6,333,031 B1 | 12/2001 | Olsson et al. | |
| 6,399,316 B1 | 6/2002 | Onda et al. | |
| 6,413,952 B1 | 7/2002 | Luengo et al. | |
| 6,429,186 B1 | 8/2002 | Fuh et al. | |

(Continued)

FOREIGN PATENT DOCUMENTS

EP        04677279 A3      1/1992

(Continued)

OTHER PUBLICATIONS

Lowman et al., J. Biol. Chemistry 266:10982-10988, 1991.*

(Continued)

*Primary Examiner*—David Romeo
*Assistant Examiner*—Daniel C Gamett
(74) *Attorney, Agent, or Firm*—Fish & Richardson P.C.

(57) ABSTRACT

The present invention provides a method of increasing neural stem cell numbers or neurogenesis by using prolactin. The method can be practiced in vivo to obtain more neural stem cells in situ, which can in turn produce more neurons or glial cells to compensate for lost or dysfunctional neural cells. The method can also be practiced in vitro to produce a large number of neural stem cells in culture. The cultured stem cells can be used, for example, for transplantation treatment of patients or animals suffering from neurodegenerative diseases or conditions. In addition, since neural stem cells are a source for olfactory neurons, the present invention also provides methods of increasing olfactory neurons and enhancing olfactory functions.

24 Claims, 4 Drawing Sheets

U.S. PATENT DOCUMENTS

| | | | |
|---|---|---|---|
| 6,551,618 B2 * | 4/2003 | Baird et al. | 424/484 |
| 6,680,295 B1 | 1/2004 | Arimura | |
| 6,797,264 B1 | 9/2004 | Eriksson | |
| 7,048,934 B2 | 5/2006 | Thompson et al. | |
| 2002/0098178 A1 | 7/2002 | Brand | |
| 2003/0049838 A1 | 3/2003 | Thompson et al. | |
| 2003/0054551 A1 | 3/2003 | Shingo et el. | |
| 2003/0054998 A1 | 3/2003 | Shingo et al. | |
| 2004/0038888 A1 | 2/2004 | Mercer et al. | |
| 2004/0092448 A1 | 5/2004 | Ohta et al. | |
| 2006/0121007 A1 | 6/2006 | Thompson et al. | |
| 2006/0148084 A1 | 7/2006 | Shingo et al. | |
| 2007/0098698 A1 | 5/2007 | Gregg et al. | |
| 2007/0179092 A1 | 8/2007 | Ohta et al. | |

FOREIGN PATENT DOCUMENTS

| | | |
|---|---|---|
| WO | WO 90 05185 | 5/1990 |
| WO | WO 93 01275 | 1/1993 |
| WO | WO 94 10292 | 5/1994 |
| WO | WO 96 09318 | 3/1996 |
| WO | WO 96 40231 | 12/1996 |
| WO | WO 97 48729 | 12/1997 |
| WO | WO 99 15191 | 4/1999 |
| WO | WO 99/21966 A | 5/1999 |
| WO | WO 99 51272 | 10/1999 |
| WO | WO 00/05260 A | 2/2000 |
| WO | WO 00/13650 A | 3/2000 |
| WO | WO 00 30675 | 6/2000 |
| WO | WO 0030675 | 6/2000 |
| WO | WO 0030675 A2 * | 6/2000 |
| WO | WO 03 018782 | 3/2003 |
| WO | WO 03 024472 | 3/2003 |
| WO | WO 03 092716 | 3/2003 |
| WO | WO 03 040310 | 5/2003 |
| WO | WO 03/092716 | 11/2003 |

OTHER PUBLICATIONS

Dubey et al., Life Sci. vol. 32, Issue 16, Apr. 18, 1983, pp. 1857-1863; abstract.*
Mulloy et al., Biol. Neonate. 1979;36(3-4):148-53;; abstract.*
Kovacs et al., Movement Disorder 18(8); 938-942, 2003.*
Studer et al., J. Neuroscience 201(19):7377-7383, Oct. 1, 2000.*
Gage, F. H., "Mammalian neural stem cells", Science, 287(5457):1433-1438 (2000).
Phelps, C.J. et al., "Pituitary hormones as neurotrophic signals: Update on hypothalamic differentiation in genetic models of altered feedback", Proceedings of the Society for Experimental Biology and Medicine, 222(1):39-58 (1999).
Phelps, C.J, et al., "Stimulatory effect of human, but not bovie, growth hormone expression on numbers of tuberoinfundibular dopaminergic neurons in transgenic mice", Endocrinology, 138(7):2849-2855 (1997).
Dicco-Bloom et al., "The PACAP Ligand/Receptor System Regulates Cerebral Cortical Neurogenisis", Annals of the New York Academy of Sciences, pp. 274-289 (1998).
Lee et al., "Pituitary Adenylyl Cyclase-Activating Polypeptide Stimulates DNA Synthesis but Delays Maturation of Oligodendrocyte Progenitors", Jounal of Neuroscience, vol. 21, No. 11, pp. 3849-3859 (2001).
Bernichtein, S., et al. S179D-human PRL, a pseudophosphorylated human PRL analog, is an agonist and not an antagonist. Endocrinology 142(9):3950-3963 (2001).
DeVito, W.J., et al., "Prolactin induced expression of interleukin-1 alpha, tumor necrosis factor-alpha, and transforming growth factor-alpha in cultured astrocytes", J. Cell Biochem. 57:290-298 (1995).
Fernandez-Pol, J.A. Epidermal growth factor receptor of A431 cells. Characterization of a monoclonal anti-receptor antibody noncompetitive agonist of epidermal growth factor action. J. Biol. Chem. 260(8):5003-5011 (1985).
Freeman, M.E., et al., "Prolactin: structure, function and regulation of secretion", Physiol. Rev. 80:1523-1631 (2000).
Johnson, D.L., et al. Erythropoietin mimetic peptides and the future. Nephrol. Dial. Transplant. 15(9):1274-1277 (2000).
Kaushansky, K. Hematopoietic growth factor mimetics. Ann. N.Y. Acad. Sci. 938:131-138 (2001).
Kolb, B., et al. Nerve growth factor treatment prevents dendritic atrophy and promotes recovery of function after cortical injury. Neuroscience 76(4):1139-1151 (1997).
Lim, D.A., et al., "Noggin antagonizes BMP signaling to create a niche for adult neurogenesis", Neuron 28: 713-726 (2000).
Livnah, O., et al. Functional mimicry of a protein hormone by a peptide agonist: the EPO receptor complex at 2.8 A. Science 273(5274):464-471 (1996).
Mode, A., et al. The human growth hormone (hGH) antagonist G120RhGH does not antagonize GH in the rat, but has paradoxical agonist activity, probably via the prolactin receptor. Endocrinology 137(2):447-454 (1996).
Moro, O., et al. Maxadilan, the vasodilator from sand flies, is a specific pituitary adenylate cyclase activating peptide type I receptor agonist. J. Biol. Chem. 272(2):966-70 (1997).
Rochefort, C., et al. Enriched odor exposure increases the number of newborn neurons in the adult olfactory bulb and improves odor memory. J. Neurosci. 22(7):2679-2689 (2002).
Shingo, T., et al. Erythropoietin regulates the in vitro and in vivo production of neuronal progenitors by mammalian forebrain neural stem cells. J. Neurosci. 21(24):9733-9743 (2001).
Wrighton, N.C., et al. Small peptides as potent mimetics of the protein hormone erythropoietin. Science 273(5274):458-464 (1996).
Shingo et al. "Pregnancy-Stimulated Neurogenesis in the Adult Female Forebrain Mediated by Prolactin" Science 299:117-120 (Jan. 2003).
Shingo et al., Supporting Online Material pp. 1-10 "Pregnancy-Stimulated Neurogenesis in the Adult Female Forebrain Mediated by Prolactin" Science 299:117-120 (Jan. 2003).
Goffin et al. "Sequence-Function Relationships within the Expanding Family of Prolactin, Growth Hormone, Placental Lactogen, and Related Proteins in Mammals" Endocrine Reviews 17: 385-410 (Jan. 2007).
Moderscheim et al. "Prolactin is Involved in Glial Responses Following a Focal Injury to the Juvenile Rat Brain" Neuroscience 145: 963-973 (2007).
Arsenijevic et al., "Insulin-like growth factor-I is necessary for neural stem cell proliferation and demonstrates distinct actions of epidermal growth factor and fibroblast growth factor-2," Journal of Neuroscience, pp. 7194-7202 (2001).
Lobie et al., "Growth hormone, insulin-like growth factor I and the CNS: localization, function and mechanism of action," Growth Hormone & IGF Research, pp. S51-S56 (2000).
Johnson et al., Evaluating the Role of the Hormone Prolactin in Neuroinflammation and repair associated with experimental autoimmune encephalomyelitis; EndMS Research Conference, Banff, Alberta Canada; Dec. 10-13, 2007.
Aberg, M.A.I. et al., "Peripheral Infusion of IGF-I Selectively Induces Neurogenesis in the Adult Rat Hippocampus," J of Neuro., vol. 20, No. 8, pp. 2896-2903 (Apr. 15, 2000).
Abramsky, O. et al., "Suppressive Effect of Pregnancy on Ms and EAE," Prog. Clin. Biol. Res., pp. 399-406 (1984).
Allen, J.S. et al., "Sexual dimorphism and asymmetries in the gray-white composition of the human cerebrum," NeuroImage, vol. 18, pp. 880-894 (2003).
Anderson, M.F. et al., "Insulin-like growth factor-I and neurogenesis in the adult mammalian brain," Brain Res Dev Brain Res., vol. 134, Nos. 1-2, pp. 115-122 (Mar. 31, 2002).
Arimura, A. et al., "PACAP functions as a neurotrophic factor," Ann. NY Acad. Sci., vol. 739, pp. 228-243 (1994).
Arimura, A. et al., "Perspectives on pituitary adenylate cyclase activating polypeptide PACAP in the neuroendocrine, endocrine and nervous systems," Jap. J. Physiol., vol. 48, pp. 301-331 (1998).
Arimura, A. et al., "Tissue Distribution of PACAP as Determined by RIA: Highly Abundant in the Rat Brain Testes," Endocrinol., vol. 129, pp. 2787-2789 (1991).

Arimura, A. "Pituitary adenylate cyclase activating polypeptide PACAP: Discovery and current status of research," Regulatory Peptides, vol. 37, pp. 287-303 (1992).

Armstrong, R.C. et al., "Absence of fibroblast growth factor 2 promotes oligodendroglial repopulation of demyelinated white matter," J Neurosci., vol. 22, No. 19, pp. 8574-8585 (2002).

Arnett, H.A. et al., "TNF-α promotes proliferation of oligodendrocyte progenitors and remyelination," Nature, vol. 4, pp. 1116-1122 (2001).

Arsenijevic & Weiss "Insulin-like Growth Factor-I (IGF-I) Recruits a Distinct Population of Embryonic Neural Stem Cells," Molecular Biology of the Cell, vol. 7 (Supp), p. 1842 (Dec. 1996).

Aston, C., et al., "Transcriptional profiling reveals evidence for signaling and oligodendroglial abnormalities in the temporal cortex from patients with major depressive disorder," Mol Psychiatry vol. 10, pp. 309-322 (2005).

Bambakidis, N. C. and Miller, R. H. "Transplantation of oligodendrocyte precursors and sonic hedgehog results in improved function and white matter sparing in the spinal cords of adult rats after contusion," J Spine, vol. 4, p. 16-26 (2004).

Banks, W.A. et al., "Passage of pituitary adenylate cyclase activating polypeptide 1-27 and pituitary adenylate cyclase activating polypeptide 1-38 across the blood-brain barrier," J. Pharmacol. Exp. Ther., vol. 267, No. 2, pp. 690-696 (1993).

Bartzokis, G., et al., "Heterogeneous age-related breakdown of white matter structural integrity: implications for cortical "disconnection" in aging and Alzheimer's disease," Neurobiol Aging, vol. 25, pp. 843-851 (2004).

Bayer, S.A., "Neuron production in the hippocampus and olfactory bulb of the adult rat brain: Addition or replacement?" Ann. NY Acad. Sci., vol. 457, pp. 163-173 (1985).

Bebo, Jr., B. F. and Dveksler, G. S., "Evidence that pregnancy specific glycoproteins regulate T-Cell function and inflammatory autoimmune disease during pregnancy," Curr. Drug Targets Inflamm. & Allergy. vol. 4, pp. 231-237 (2005).

Bebo, Jr., B.F. et al., "Low-dose estrogen therapy ameliorates experimental autoimmune encephalomyelitis in two different inbred mouse strains," J. Immunol., vol. 166, pp. 2080-2089 (2001).

Brück, W. and Stadelmann, C., "The spectrum of multiple sclerosis: new lessons from pathology," Curr Opin Neurol, vol. 18, pp. 221-224 (2005).

Buckner, R.L., "Memory and executive function in aging and AD: multiple factors that cause decline and reserve factors that compensate," Neuron, vol. 44, pp. 195-208 (2004).

Camarillo, I. G. et al., "Prolactin receptor expression in the epithelia and stroma of the rat mammary gland," J Endocrinol, vol. 171, pp. 85-95 (2001).

Cao, Q. et al., "Functional recovery in traumatic spinal cord injury after transplantation of multineurotrophin-expressing glial-restricted precursor cells," J Neurosci, vol. 25, No. 30, pp. 6947-6957 (2005).

Carey, R.G. et al., "Pituitary Adenylate Cyclase Activating Polypeptide Antimitogenic Signaling in Cerebral Cortical Progenitors is Regulated by p57Kip2-dependent CDK2 activity," J. Neurosci., vol. 22, No. 5, pp. 1583-1591 (2002).

Cerghet, M. et al., "Proliferation and death of oligodendrocytes and myelin proteins are differentially regulated in male and female rodents," J Neurosci, vol. 26, No. 5, pp. 1439-1447 (2006).

Cerarni A., "Effects of Epoetin Alfa on the Central Nervous System," Seminars in Oncology, vol. 28, No. 2. Suppl 8, pp. 66-70 (Apr. 2001).

Chikanza, I. C., "Prolactin and neuroimmunomodulation: in vitro and in vivo observations," Ann. N.Y. Acad. Sci., vol. 876, pp. 119-130 (1999).

Chojnacki, A. and Weiss, S., "Isolation of a novel platelet-derived growth factor-responsive precursor from the embryonic ventral forebrain," J. Neurosci., vol. 24, No. 48, pp. 10888-10899 (2004).

Christophe, J. "Type I Receptors for PACAP (a neuropeptide even more important than VIP?)" Biochim. Biophys. Acta, vol. 1154, pp. 183-199 (1993).

Confavreux, C. et al., "Rate of pregnancy-related relapse in multiple sclerosis," N Engl J Med., vol. 339, No. 5, pp. 285-291 (1998).

Craig, C.G. et al., "In vivo growth factor expansion of endogenous subependymal neural precursor cell populations in adult mouse brain," J. Neurosci., vol. 16, No. 8, pp. 2649-2658 (1996).

Cunningham, B. C., et al., "High-resolution epitope mapping of hGH-receptor interactions by alanine-scanning mutagenesis," Sci., vol. 244, p. 1282-1085 (1989).

Cunningham, B.C. et al., "Receptor and antibody epitopes in human growth hormone identified by homolog-scanning mutagenesis," Sci., vol. 243, No. 4896, pp. 1330-1336 (1989).

Dawson, M.R.L. et al., "NG2-expressing glial progenitor cells an abundant and widespread population of cycling cells in the adult rat CNS," Mol Cell Neurosci, vol. 24, pp. 476-488 (2003).

Dong, W. K. and Greenough W. T., "Plasticity of nonneuronal brain tissue: roles in developmental disorders," Ment Retard Dev Disabil Res. Rev., vol. 10, pp. 85-90 (2004).

Draca, S. and Levic, X. "The possible role of prolactin in the immunopathogenesis of multiple sclerosis," Med. Hypotheses, vol. 47, pp. 89-92 (1996).

Faulkner, J. and Keirstead, H. S., "Human embryonic stem cell-derived oligodendrocyte progenitors for the treatment of spinal cord injury," Transpl. Immunol., vol. 15, pp. 131-142 (2005).

Ferro, J. M. and Madureira, S. "Age-related white matter changes and cognitive impairment," J Neurol Sci., vols. 203-204, pp. 221-225 (2002).

Fields, R.D., "Myelination: an overlooked mechanism of synaptic plasticity?" Neuroscientist, vol. 11, No. 6 pp. 528-531 (2005).

Fleming, A. S. and Walsh, C., "Neuropsychology of maternal behavior in the rat: c-fos expression during mother-litter interactions," Psychoneuroendocrinology vol. 19, Nos. 5-7, pp. 429-443 (1994).

Freed, C.R. et al., "Survival of Implanted Fetal Dopamine Cells and Neurologic Improvement 12 to 46 Months After Transplantation for Parkinson's Disease," N. Engl. J. Med., vol. 327, No. 22, pp. 1549-1555 (1992).

Gage, F.H. et al., "Isolation, characterization, and use of stem cells from the CNS," Annu Rev Neurosci., vol. 18, pp. 159-192 (1995).

Gage, F.H. et al., "Survival and differentiation of adult neuronal progenitor cells transplanted to the adult brain," Proc Natl Acad Sci., vol. 92, pp. 11879-11883 (Dec. 5, 1995).

Gatewood, J. D. et al., "Motherhood mitigates aging-related decrements in learning and memory and positively affects brain aging in the rat," Brain Res Bull, vol. 66, pp. 91-98 (2005).

Gensert, J. M. and Goldman J. E., "In vivo characterization of endogenous proliferating cells in adult rat subcortical white matter," GLIA, vol. 17, pp. 39-51 (1996).

Gensert, J. M. and Goldman, J. E., "Endogenous progenitors remyelinate demyelinated axons in the adult CNS," Neuron, vol. 19, pp. 197-203 (1997).

Goeddel, D.V. et al., "Direct expression in *Escherichia coli* of a DNA sequence coding for human growth hormone" Nature, vol. 281, No. 5732, pp. 544-548 (1979).

Goffin V. et al., "Sequence-Function Relationships within the Expanding Family of Prolactin, Growth Hormone, Placental Lactogen, and Related Proteins in Mammals," Endocrine Reviews 17, No. 4, pp. 385-410 (Jan. 2007).

Gray, G.L., et al., Periplasmic production of correctly processed human growth hormone in *Escherichia coli*: natural and bacterial signal sequences are interchangeable. Gene, vol. 39, Nos. 2-3, pp. 247-254 (1985).

Gur, R. C. et al., "Sex differences in brain gray and white matter in healthy young adults: correlations with cognitive performance," J Neurosci, vol. 19, No. 10, pp. 4065-4072 (1999).

Hack, M. A. et al., "Neuronal fate determinants of adult olfactory bulb neurogenesis," Nat Neurosci, vol. 8, No. 7, pp. 865-872 (2005).

Haier, R.J. et al., "The neuroanatomy of general intelligence: sex matters," Neuroimage vol. 25, pp. 320-327 (2005).

Hansel, D.E. et al., "Regulation of Olfactory Neurogenesis by Amidated Neuropeptides," J. Neurosci. Res. vol. 66, pp. 1-7 (2001).

Hashimoto, H. et al., "Altered Psychomotor Behaviors in Mice Lacking Pituitary Adenylate Cyclase-Activating Polypeptide (PACAP)," PNAS, vol. 98, No. 23, pp. 13355-13360 (2001).

Hashimoto H. et al., "Molecular Cloning and Tissue Distribution of a Receptor for Pituitary Adenylate Cyclase Activating Polypeptide," Neuron, vol. 11, pp. 333-342 (1993).

Hirose, M. et al., "Gene expression of PACAP and its receptors in the ES cell-derived neuronal stem cells," Japanese Journal of Pharmacology, The Japanese Pharmacological Society, Kyoto, JP, vol. 88, Suppl. 1, p. 143, 2002.

Inzitari, D., "Leukoaraiosis: An independent risk factor for stroke?" Stroke, vol. 34, pp. 2067-2071 (2003).

Ito, A. et al., "Estrogen treatment down-regulates TNF-α production and reduces the severity of experimental autoimmune encephalomyelitis in cytokine knockout mice," J Immunol, vol. 167, pp. 542-552 (2001).

Jokinen, H. et al., "Medial temporal lobe atrophy and memory deficits in elderly stroke patients," Eur J Neurol 11:825-832 (2004).

Kandel, "Principles of Neural Science," 1991, p. 981.

Kaplan, M.S., "Neurogenesis in the 3-month Old Rat Visual Cortex," J. Comp. Neurol., vol. 195, pp. 323-338 (1981).

Karimi-Abdolrezaee, S. et al., "Delayed transplantation of adult neural precursor cells promotes remyelination and functional neurological recovery after spinal cord injury," Neurosci., vol. 26, No. 13, pp. 3377-3389 (2006).

Keirstead, H.S. et al., "Human embryonic stem cell-derived oligodendrocyte progenitor cell transplants remyelinate and restore locomotion after spinal cord injury," J Neurosci., vol. 25, No. 19, pp. 4694-4075 (2005).

Kieseier, B.C. et al., "Multiple sclerosis-novel insights and new therapeutic strategies," Curr Opin Neurol., vol. 18, pp. 211-220 (2005).

Kim, J. H. and Juraska, J. M., "Sex differences in the development of axon number in the splenium of the rat corpus callosum from postnatal day 15 through 60," Brain Res. Dev. Brain Res., vol. 102, p. 77-85 (1997).

Kim, S. et al., "Estriol ameliorates autoimmune demyelinating disease: implications for multiple sclerosis," Neurology, vol. 52, pp. 1230-1238 (1999).

Kimura, C. et al., "A Novel Peptide Which Stimulates Adenylate Cyclase: Molecular Cloning and Characterization of the Ovine and Human cDNAs," Biochem. Biophys. Res. Comm., vol. 166, pp. 81-89 (1990).

Kinsley, C. H. et al., "Motherhood improves learning and memory" Nature, vol. 402, p. 137 (1999).

Konishi, Y. et al., "Trophic effect of erythropoietin and other hematopoietic factors on central cholinergic neurons into vitro and in vivo" Brain Research vol. 609, pp. 29-35 (1993).

Kovacs, T. et al., "Olfactory Bulb in Multiple System Atrophy", Movement Disorder, vol. 18, No. 8, pp. 938-942 (2003).

Lambert, K. G. et al., "Pup exposure differentially enhances foraging ability in primiparous and nulliparous rats" Physiol. Behav., vol. 84, pp. 799-806 (2005).

Learish, R.D. et al., "Intraventricular transplantation of oligodendrocyte progenitors into a fetal myelin mutant results in widespread formation of myelin" Ann Neurol, vol. 46, pp. 716-722 (1999).

Lee, K. H. et al., "Effects of glial transplantation on functional recovery following acute spinal cord injury" J. Neurotrauma, vol. 22, No. 5, 575-589, (2005).

Lelievre, V. et al., "Cross-talk between PACAP and sonic hedgehog (SHH) pathways in neural stem cells, cerebellar granular progenitor cells and oligodendrocyte progenitors to control cell fate and proliferation." Regulatory Peptides, vol. 115, No. 1, p. 50 (2003) (abstract).

Lelievre, V. et al., "Fibroblast growth factor-2 converts PACAP growth action on embryonic hindbrain precursors from stimulation to inhibition." Journal of Neuroscience Research, vol. 67, No. 5, pp. 566-573 (Mar. 1, 2002).

Lelievre, V. et al., "Interactive of PACAP with sonic Hedgehog on neural stem cell and oligodendrocyte progenitor proliferation." J of Neurochemistry, vol. 85, Supp 1, p. 66 (May 20, 2003).

Levine, J. M. et al., "The oligodendrocyte precursor cell in health and disease" Trends Neurosci., vol. 24, No. 1, pp. 39-47 (2001).

Levison, S.W. et al., "Cycling cells in the adult rat neocortex preferentially generate oligodendroglia" J Neurosci Res., vol. 57, pp. 435-466 (1999).

Lindholm et al., "Developmental Regulation of Pituitary Adenylate Cyclase Activating Polypeptide (PACAP) and its Receptor 1 in Rat Brain: Function of PACAP as a Neurotrophic Factor," Ann. N.Y. Acad. Sci., vol. 865, pp. 189-196 (1998).

Lledo, P. M. et al., "Adult neurogenesis and functional plasticity in neuronal circuits," Nat Rev Neurosci, vol. 7, pp. 179-193 (2006).

Love, G. et al., "Maternal experience produces long-lasting behavioral modification in the rat," Behav Neurosci., vol. 119, No. 4, pp. 1084-1096 (2005).

Lu, N. et al., "Pituitary Adenylate Cyclase-Activating Polypeptide is an Autocrine Inhibitor of Mitosis in cultured Cortical Precursor Cells," Proc. Natl. Acad. Sci., vol. 94, pp. 3357-3362 (1997).

Lubetzki, C. et al., "Promoting repair in multiple sclerosis: problems and prospects," Curr Opin Neurol., vol. 18, pp. 237-244 (2005).

Lyoo, I.K. et al., "White matter hyperintensities on magnetic resonance imaging of the brain in children with psychiatric disorders," Compr Psychiatry, vol. 43, No. 5, pp. 361-368 (2002).

Mack, C. M. et al., "Sex differences in the distribution of axon types within the genu of the rat corpus callosum," Brain Res, vol. 697, pp. 152-156, 1995.

Menn, B. et al., "Origin of oligodendrocytes in the subventricular zone of the adult brain," J Neurosci., vol. 26, No. 30, pp. 7907-7918 (2006).

Miyata, A. et al., "Isolation of a Novel 38 Residue-Hypothalamic Polypeptide which Stimulates Adenylate Cyclase in Pituitary Cells," Biochem. Bophys. Res. Comm. 164:567-574 (1989).

Moderscheim, T.A.E., et al., "Prolactin is Involved in Glial Responses Following a Focal Injury to the Juvenile Rat Brain" Neuroscience 145: 963-973 (2007).

Moore, P.B. et al., "Cerebral white matter lesions in bipolar affective disorder: relationship to outcome," Br J Psychiatry, vol. 178, pp. 172-176 (2001).

Mori, E. "Impact of subcortical ischemic lesions on behavior and cognition" Ann. N. Y. Acad Sci., vol. 977, p. 141-148 (2002).

Nait-Oumesmar, B., et al., "Progenitor cells of the adult mouse subventricular zone proliferate, migrate and differentiate into oligodendrocytes after demyelination" Eur J Neurosci., vol. 11, pp. 4357-4366 (1999).

Neumann, I. D., "Alterations in behavioral and neuroendocrine stress coping strategies in pregnant, parturient and lactating rats," Prog. Brain Res., vol. 133, pp. 143-152 (2001).

Nicot, A. et al., "Regulation of Neuroblast Mitosis is Detemined by PACAP Receptor Isoform Expression," PNAS, vol. 98, No. 8, pp. 4758-4763 (2001).

Nuñez, J. L. et al., "Myelination in the splenium of the corpus callosum in adult male and female rats," Dev Brain Res., vol. 120, pp. 87-90 (2000).

Nyberg, F. "Aging effects on growth hormone receptor binding in the brain," Exp. Gerontol, vol. 32, Nos. 4-5, pp. 521-528 (1997).

Nyberg, F., "Growth hormone in the brain: characteristics of specific brain targets for the hormone and their functional significance," Front Neuroendocrinol., vol. 21, pp. 330-348 (2000).

Ohta S. and Weiss, S., "Pituitary adenylate cyclase-activating polypeptide (PACAP) regulates forebrain neural stem cell fate in vitro and in vivo," Society for Neuroscience Abstract Viewer and Itinerary Planner, vol. 329, No. 13, 2002 (abstract).

Ormandy, C. J. et al., "Null mutation of the prolactin receptor gene produces multiple reproductive defects in the mouse" Genes Dev., vol. 11, pp. 167-178 (1997).

Otto, C. et al., "Altered Emotional Behavior in PACAP-type-I-receptor-deficient Mice," Brain Res. Mol. Brain Res. 91(1-2):78-84 (2001).

Perlow et al., "Brain Grafts Reduce Motor Abnormalities Produced by Destruction of Nigrostriatal Dopamine System," Sci., vol. 204, pp. 643-647 (1979).

Pesce, M. et al., "Pituitary adenylate cyclass-activating polypeptide (PACAP) stimulates adenylate cyclase and promotes proliferation of mouse primordial germ cells." Development (Cambridge), vol. 122, No. 1, pp. 215-221 (1996).

Peters, A. and Sethares C., "Oligodendrocytes, their progenitors and other neuroglial cells in the aging primate cerebral cortex" Cereb Cortex, vol. 14, pp. 995-1007 (2004).

Peters, A. et al., "Effects of aging on the neuroglial cells and pericytes within area 17 of the rhesus monkey cerebral cortex" Anat Rec, vol. 229, pp. 384-398 (1991).

Peters, A. J., "The effects of normal aging on myelin and nerve fibers: a review," J Neurocytol, vol. 31, pp. 581-593 (2002).

Picard-Riera, N. et al., "Experimental autoimmune encephalomyelitis mobilizes neural progenitors from the subventricular zone to undergo oligodendrogenesis in adult mice," PNAS, vol. 99, No. 20, pp. 13211-13216 (2002).

Polito, A. and Reynolds, R., "NG2 expressing cells as oligodendrocyte progenitors in the normal and demyelinated adult central nervous system," Anat., vol. 207, pp. 707-716 (2005).

Potten, C.S. and Loeffler, M., "Stem Cells: Attributes, Cycles, Spirals, Pitfalls and Uncertainties. Lessons for and from the Crypt," Development, vol. 110, pp. 1001-1020 (1990).

Rakic, "Limits of Neurogenesis in Primates," Science 227:1054-1056 (1985).

Rawlings, S.R., "At the Cutting Edge PACAP, PACAP Receptors, and Intracellular Signalling," Mol. and Cellular Endocrinol., vol. 191, pp. C5-C9 (1994).

Reynolds, B.A. and Weiss, S., "Generation of Neurons and Astrocytes from Isolated Cells of the Adult Mammalian Central Nervous System," Sci., vol. 255, pp. 1707-1710 (1992).

Rietze, R. et al., "Mitotically Active Cells that Generate Neurons and Astrocytes are Present in Multiple Regions of the Adult Mouse Hippocampus," J. Comp. Neurol., vol. 424, No. 3, pp. 397-408 (2000).

Rostene, W. et al., "VIP and PAGAP via G-Protein coupled receptors are potent inducers of mouse embryonic stem cell neuronal differentiation," Regulatory Peptides, vol. 115, No. 1, p. 55. (2003).

Scheepens, A. et al., "Growth Hormone as a Neuronal Rescue Factor During Recovery from CNS Injury," Neuroscience, vol. 104, No. 3, pp. 677-687 (Jun. 14, 2001).

Schlessinger, J. et al., "Crystal Structure of a Ternary FGF-FGFR-Heparin Complex Reveals a Dual Role for Heparin in FGFR Binding Dimerization," Molecular Cell, vol. 6, No. 3, pp. 743-750 (Sep. 2000).

Schradin, C. and Anzenberger G., "Prolactin, the Hormone of Paternity" News Physiol Sci., vol. 14, pp. 223-231 (1999).

Scolding, N. J. and Franklin, R. J. M., "Remyelination in demyelinating disease" Baillieres Clin Neurol., vol. 6(3), pp. 525-548 (1997).

Shimazaki, T., et al., "The ciliary neurotrophic factodleukemia inhibitory factor/gp130 receptor complex operates in the maintenance of mammalian forebrain neural stem cells," J. Neurosci. 21(19):7642-7653 (2001).

Shingo, T. et al., "Pregancy-Stimulated Neurogenesis in the Adult Female Forebrain Mediated by Prolactin," Sci., vol. 229, pp. 117-120 (2003) (including Supporting Online Material (1-10 pages)).

Shioda, J. et al., "Pleiotropic functions of PACAP in the CNS. Neuroprotection and neurodevelopment," Ann. NY Acad. Sci., vol. 1070, pp. 550-560 (2006).

Sicotte, N. L. et al., "Treatment of multiple sclerosis with the pregnancy hormone estriol," Ann Neurol., vol. 52, pp. 421-428 (2002).

Silverstone, T. et al., "Deep white matter hyperintensities in patients with bipolar depression, unipolar depression and age-matched control subjects," Bipolar Disord, vol. 5, pp. 53-57 (2003).

Sirevaag, A. M. and Greenough, W. T., "Differential rearing effects on rat visual cortex synapses. III. Neuronal and glial nuclei, boutons, dendrites and capillaries," Brain Res., vol. 424, pp. 320-332 (1987).

Sorokan, et al., "Erythropoietin mediates increased neurogenesis by embryonic CNS stem cells following a modest hypoxic insult," Society for Neuroscience Abstracts, 23(1/2):320 (1997).

Spencer, D.D. et al., "Unilateral Transplantation of Human Fetal Mesencephalic Tissue into the Caudate Nucleus of Patients with Parkinson's Disease," New Engl. J. Med., vol. 327, No. 22, pp. 1541-1548 (1992).

Stangel, M. and Hartung H-P., "Remyelinating strategies for the treatment of multiple sclerosis," Prog Neurobiol., vol. 68, pp. 361-376 (2002).

Stevens, B. et al., "Adenosine: a neuron-glial transmitter promoting myelination in the CNS in response to action potentials," Neuron, vol. 36, pp. 855-868 (2002).

Sturrock, R. R. "Myelination of the mouse corpus callosum," Neuropathol Appl Neurobiol., vol. 6, pp. 415-420 (1980).

Szeligo, F. and Leblond, C. P., "Response of the three main types of glial cells of cortex and corpus callosum in rats handled during suckling or exposed to enriched, control and impoverished environments following weaning," J. Comp. Neurol., vol. 172, pp. 247-263 (1977).

Tang, D. G. et al., "Long-term culture of purified postnatal oligodendrocyte precursor cells. Evidence for an intrinsic maturation program that plays out over months," J. Cell Biol., vol. 148, pp. 971-984 (2000).

Tauber, H. et al., "Myelination in rabbit optic nerves is accelerated by artificial eye opening," Neuroci Lett., vol. 16, pp. 235-238 (1980).

The American Heritage Dictionary of the English Language 4th Ed., Dictionary.com/neural (2000).

Totoiu, M. O. and Keirstead, H. S., "Spinal cord injury is accompanied by chronic progressive demyelination," J Comp Neurol., vol. 486, pp. 373-383 (2005).

Tropepe, V. et al., "Transforming growth factor-α null and senescent mice show decreased neural progenitor cell proliferation in the forebrain subependyma," J. Neurosci., vol. 17, Issue 20, pp. 7850-7859 (1997).

Van Der Kooy and Weiss, "Why Stem Cells?" Sci. vol. 287, pp. 1439-1441 (2000).

Van Walderveen et al., "Magnetic resonance evaluation of disease activity during pregnancy in multiple sclerosis," Neurology, vol. 44, pp. 327-329 (1994).

Vaudry, D. et al., "Neurotrophic activity of pituitary adenylate cyclase-activating polypeptide on rate cerebellar cortex during development," Proc. of the Nat. Acad. of Sci., vol. 96, No. 16, pp. 9415-9420 (Aug. 3, 1999).

Vaudry, D. et al., "Pituitary adenylate cyclase-activating polypeptide and its receptors from structure to functions," Pharmacol. Rev., vol. 52, No. 2, pp. 269-324 (2000).

Voskuhl, R. R., "Hormone-based therapies in MS" Int. MS J, vol. 10, pp. 60-66 (2003).

Walker, C. D. et al., "Mother to infant or infant to mother? Reciprocal regulation of responsiveness to stress in rodents and the implications for humans," J. Psy. Neurosci. vol. 29, No. 5, pp. 364-382 (2004).

Wardlaw, J.M. et al., "Is diffusion imaging appearance an independent predictor of outcome after ischemic stroke?" Neurology, vol. 59, pp. 1381-1387 (2002).

Waschek, J.A., "Multiple actions of pituitary adenylyl cyclase activating peptide in nervous system development and regeneration," Develop. Neuro., Viol. 24, pp. 14-23, (2002).

Waschek, J.A., "VIP and PACAP Receptor-mediated actions on cell proliferation and survival," Ann. N.Y. Acad. Sci., vol. 805, pp. 290-301 (1996).

Weetman A. P., "The immunology of pregnancy," Thyroid, vol. 9, No. 7, pp. 643-646 (1999).

Whittemore S.R., et al., "Mitogen and substrate differentially affect the lineage restriction of adult rat subventricular zone neural precursor cell populations," Exp. Cell. Res., vol. 252, No. 1, pp. 75-95 (Oct. 10, 1999).

Widner, H. et al., "Bilateral fetal mesencephalic grafting into two patients with parkinsonism induced by l-methyl-4-phenyl- 1,2,3,6-tetrahydropyridine (MPTP)," N. Engl. J. Med. vol. 327, pp. 1556-1563 (1992).

Wu, H. Y. et al., "Expression of QKI proteins and MAP1B identifies actively myelinating oligodendrocytes in adult rat brain," Mol. Cell. Neurosci., vol. 17, pp. 292-302 (2001).

Yuhara, A. et al., "PACAP has a Neurotrophic effect on cultured basal forebrain cholinergic neurons from adult rats," Dev. Brain Res., vol. 131, No. 1, pp. 41-45 (2001).

* cited by examiner

PROLACTIN INDUCED INCREASE IN NEURAL STEM CELL NUMBERS

RELATED APPLICATIONS

This application claims the benefit of U.S. Provisional Applications Ser. No. 60/322,514, filed Sep. 14, 2001, and Ser. No. 60/386,404, filed Jun. 7, 2002. The entire disclosure of each of these priority applications is hereby incorporated by reference.

FIELD OF THE INVENTION

The present invention relates to methods of increasing neural stem cell numbers, neurogenesis or new olfactory neuron numbers by using prolactin, as well as methods for treating or ameliorating neurodegenerative diseases or conditions.

REFERENCES

U.S. Patent Application Publication No. 2002 0098178 A1.
U.S. Pat. No. 5,023,252.
U.S. Pat. No. 5,128,242.
U.S. Pat. No. 5,198,542.
U.S. Pat. No. 5,208,320.
U.S. Pat. No. 5,268,164.
U.S. Pat. No. 5,326,860.
U.S. Pat. No. 5,506,107.
U.S. Pat. No. 5,506,206.
U.S. Pat. No. 5,527,527.
U.S. Pat. No. 5,547,935.
U.S. Pat. No. 5,614,184.
U.S. Pat. No. 5,623,050.
U.S. Pat. No. 5,686,416.
U.S. Pat. No. 5,723,115.
U.S. Pat. No. 5,750,376.
U.S. Pat. No. 5,773,569.
U.S. Pat. No. 5,801,147.
U.S. Pat. No. 5,833,988.
U.S. Pat. No. 5,837,460.
U.S. Pat. No. 5,851,832.
U.S. Pat. No. 5,885,574.
U.S. Pat. No. 5,955,346.
U.S. Pat. No. 5,977,307.
U.S. Pat. No. 5,980,885.
U.S. Pat. No. 6,015,555.
U.S. Pat. No. 6,048,971.
U.S. Pat. No. 6,191,106.
U.S. Pat. No. 6,242,563.
U.S. Pat. No. 6,329,508.
U.S. Pat. No. 6,333,031.
U.S. Pat. No. 6,413,952.
U.S. Pat. No. 6,429,186.
WO 96 40231.
WO 97 48729.

Bernichtein, S., et al. S179D-human PRL, a pseudophosphorylated human PRL analog, is an agonist and not an antagonist. Endocrinology 142(9):3950-3963 (2001).

DeVito, W. J., et al., "Prolactin induced expression of interleukin-1 alpha, tumor necrosis factor-alpha, and transforming growth factor-alpha in cultured astrocytes", J. Cell Biochem. 57:290-298 (1995).

Fernandez-Pol, J. A. Epidermal growth factor receptor of A431 cells. Characterization of a monoclonal anti-receptor antibody noncompetitive agonist of epidermal growth factor action. J. Biol. Chem. 260(8):5003-5011 (1985).

Freeman, M. E., et al., "Prolactin: structure, function and regulation of secretion", Physiol. Rev. 80:1523-1631 (2000).

Johnson, D. L., et al. Erythropoietin mimetic peptides and the future. Nephrol. Dial. Transplant. 15(9):1274-1277 (2000).

Kaushansky, K. Hematopoietic growth factor mimetics. Ann. N.Y. Acad. Sci. 938:131-138 (2001).

Kolb, B., et al. Nerve growth factor treatment prevents dendritic atrophy and promotes recovery of function after cortical injury. Neuroscience 76(4):1139-1151 (1997).

Lim, D. A., et al., "Noggin antagonizes BMP signaling to create a niche for adult neurogenesis", Neuron 28: 713-726 (2000).

Livnah, O., et al. Functional mimicry of a protein hormone by a peptide agonist: the EPO receptor complex at 2.8 A. Science 273(5274):464-471 (1996).

Mode, A., et al. The human growth hormone (hGH) antagonist G120RhGH does not antagonize GH in the rat, but has paradoxical agonist activity, probably via the prolactin receptor. Endocrinology 137(2):447-454 (1996).

Moro, O., et al. Maxadilan, the vasodilator from sand flies, is a specific pituitary adenylate cyclase activating peptide type I receptor agonist. J. Biol. Chem. 272(2):966-70 (1997).

Rochefort, C., et al. Enriched odor exposure increases the number of newborn neurons in the adult olfactory bulb and improves odor memory. J. Neurosci. 22(7):2679-2689 (2002).

Shingo, T., et al. Erythropoietin regulates the in vitro and in vivo production of neuronal progenitors by mammalian forebrain neural stem cells. J. Neurosci. 21(24):9733-9743 (2001).

Wrighton, N. C., et al. Small peptides as potent mimetics of the protein hormone erythropoietin. Science 273(5274):458-464 (1996).

All of the publications, patents and patent applications cited above or elsewhere in this application are herein incorporated by reference in their entirety to the same extent as if the disclosure of each individual publication, patent application or patent was specifically and individually indicated to be incorporated by reference in its entirety.

BACKGROUND OF THE INVENTION

In recent years, neurodegenerative disease has become an important concern due to the expanding elderly population which is at greatest risk for these disorders. Neurodegenerative diseases include the diseases which have been linked to the degeneration of neural cells in particular locations of the central nervous system (CNS), leading to the inability of these cells to carry out their intended function. These diseases include Alzheimer's Disease, Multiple Sclerosis (MS), Huntington's Disease, Amyotrophic Lateral Sclerosis, and Parkinson's Disease. In addition, probably the largest area of CNS dysfunction (with respect to the number of affected people) is not characterized by a loss of neural cells but rather by abnormal functioning of existing neural cells. This may be due to inappropriate firing of neurons, or the abnormal synthesis, release, and processing of neurotransmitters. These dysfunctions may be the result of well studied and characterized disorders such as depression and epilepsy, or less understood disorders such as neurosis and psychosis. Moreover, brain injuries often result in the loss of neural cells, the inappropriate functioning of the affected brain region, and subsequent behavior abnormalities.

Consequently, it is desirable to supply neural cells to the brain to compensate for degenerate or lost neurons in order to treat neurodegenerative diseases or conditions. One approach to this end is to transplant neural cells into the brain of the patient. This approach requires a source of large amounts of neural cells, preferably from the same individual or a closely related individual such that host-versus-graft or graft-versus-host rejections can be minimized. As it is not practical to remove a large amount of neurons or glial cells from one person to transplant to another, a method to culture large quantity of neural cells is necessary for the success of this approach.

Another approach is to induce the production of neural cells in situ to compensate for the lost or degenerate cells. This approach requires extensive knowledge about whether it is possible to produce neural cells in brains, particularly adult brains, and how.

The development of techniques for the isolation and in vitro culture of multipotent neural stem cells (for example, see U.S. Pat. Nos. 5,750,376; 5,980,885; 5,851,832) significantly increased the outlook for both approaches. It was discovered that fetal brains can be used to isolate and culture multipotent neural stem cells in vitro. Moreover, in contrast to the long time belief that adult brain cells are not capable of replicating or regenerating brain cells, it was found that neural stem cells may also be isolated from brains of adult mammals. These stem cells, either from fetal or adult brains, are capable of self-replicating. The progeny cells can again proliferate or differentiate into any cell in the neural cell lineage, including neurons, astrocytes and oligodendrocytes. Therefore, these findings not only provide a source of neural cells which can be used in transplantations, but also demonstrate the presence of multipotent neural stem cells in adult brain and the possibility of producing neurons or glial cells from these stem cells in situ.

It is therefore desirable to develop methods of efficiently producing neural stem cells for two purposes: to obtain more stem cells and hence neural cells which can be used in transplantation therapies, and to identify methods which can be used to produce more stem cells in situ.

SUMMARY OF THE INVENTION

The present invention provides a method of increasing neural stem cell numbers by using prolactin. The method can be practiced in vivo to obtain more neural stem cells in situ, which can in turn produce more neurons or glial cells to compensate for lost or dysfunctional neural cells. The method can also be practiced in vitro to produce a large number of neural stem cells in culture. The cultured stem cells can be used, for example, for transplantation treatment of patients or animals suffering from or suspected of having neurodegenerative diseases or conditions.

Accordingly, one aspect of the present invention provides a method of increasing neural stem cell number, comprising providing an effective amount of a prolactin to at least one neural stem cell under conditions which result in an increase in the number of neural stem cells. The neural stem cell may be located in the brain of a mammal, in particular in the subventricular zone of the brain of the mammal. Preferably, the prolactin is administered to the ventricle of the brain. Although mammals of all ages can be subjected to this method, it is preferable that the mammal is not an embryo. More preferably, the mammal is an adult.

The mammal may suffer from or be suspected of having a neurodegenerative disease or condition. The disease or condition may be a brain injury, such as stroke or an injury caused by a brain surgery. The disease or condition may be aging, which is associated with a significant reduction in the number of neural stem cells. The disease or condition can also be a neurodegenerative disease, particularly Alzheimer's disease, multiple sclerosis, Huntington's disease, amyotrophic lateral sclerosis, or Parkinson's disease.

Alternatively, the neural stem cell may be in a culture in vitro.

Whether the prolactin is used in vivo or in vitro, other factors may be applied in combination with the prolactin, such as erythropoietin, cyclic AMP, pituitary adenylate cyclase activating polypeptide (PACAP), serotonin, bone morphogenetic protein (BMP), epidermal growth factor (EGF), transforming growth factor alpha (TGFα), fibroblast growth factor (FGF), estrogen, growth hormone, insulin-like growth factor 1, and/or ciliary neurotrophic factor (CNTF). The prolactin may be any prolactin analog or variant which is capable of inducing an increase in the stem cell number. Preferably, the prolactin is a mammalian prolactin, most preferably a human prolactin.

Another aspect of the present invention provides a method of treating or ameliorating a neurodegenerative disease or condition in a mammal, comprising providing an effective amount of a prolactin to the brain of the mammal. The disease or condition may be a brain injury, such as stroke or an injury caused by a brain surgery. The disease or condition may be aging, which is associated with a significant reduction in the number of neural stem cells. The disease or condition can also be a neurodegenerative disease, particularly Alzheimer's disease, multiple sclerosis, Huntington's disease, amyotrophic lateral sclerosis, or Parkinson's disease.

The mammal can optionally receive a transplantation of neural stem cells and/or neural stem cell progeny. The transplantation may take place before, after, or at the same time the mammal receives the prolactin. Preferably, the mammal receives the transplantation prior to or concurrently with the prolactin.

The mammal can optionally receive at least one additional factor, such as erythropoietin, cyclic AMP, pituitary adenylate cyclase activating polypeptide (PACAP), serotonin, bone morphogenetic protein (BMP), epidermal growth factor (EGF), transforming growth factor alpha (TGFα), fibroblast growth factor (FGF), estrogen, growth hormone, insulin-like growth factor 1, and/or ciliary neurotrophic factor (CNTF).

The prolactin and/or the additional factor can be provided by any method established in the art. For example, they can be administered intravascularly, intrathecally, intravenously, intramuscularly, subcutaneously, intraperitoneally, topically, orally, rectally, vaginally, nasally, by inhalation or into the brain. The administration is preferably performed systemically, particularly by subcutaneous administration. The prolactin or additional factor can also be provided by administering to the mammal an effective amount of an agent that can increase the amount of endogenous prolactin or the additional factor in the mammal. For example, the level of prolactin in an animal can be increased by using prolactin releasing peptide.

When prolactin or any additional factor is not directly delivered into the brain, a blood brain barrier permeabilizer can be optionally included to facilitate entry into the brain. Blood brain barrier permeabilizers are known in the art and include, by way of example, bradykinin and the bradykinin agonists described in U.S. Pat. Nos. 5,686,416; 5,506,206 and 5,268,164 (such as $NH_2$-arginine-proline-hydroxyproxyproline-glycine-thienylalanine-serine-proline-4-Me-tyrosineψ ($CH_2NH$)-arginine-COOH). Alternatively, the factors can be conjugated to the transferrin receptor antibodies as described in U.S. Pat. Nos. 6,329,508; 6,015,555; 5,833,988 or 5,527,527. The factors can also be delivered as a fusion protein comprising the factor and a ligand that is reactive with a brain capillary endothelial cell receptor, such as the transferrin receptor (see, e.g., U.S. Pat. No. 5,977,307).

Another aspect of the present invention provides a method of enhancing neuron formation from neural stem cells, comprising providing a prolactin to at least one neural stem cell under conditions that result in enhanced neuron formation from said neural stem cell. Further provided is a method of increasing new neuron formation in the olfactory bulb of a mammal, comprising providing an effective amount of a prolactin to the mammal. Compositions and pharmaceutical compositions comprising a prolactin and at least one additional factor are also provided.

Further aspects of the present invention provide compositions and pharmaceutical compositions useful in the present invention, comprising a prolactin and optionally an additional factor. The compositions or pharmaceutical compositions preferably comprise prolactin and erythropoietin, prolactin and EGF, or prolactin and PACAP.

BRIEF DESCRIPTION OF THE DRAWINGS

FIG. 2. The effects of prolactin infusion. PRL: prolactin; VEH: vehicle; PRP:
PRL-releasing peptide; 2W: 2 weeks; 4W: 4 weeks. *$p<0.05$.
(A) Prolactin infusion increased BrdU-labeled cells in the forebrain SVZ via both subcutaneous and intracerebroventricular routes.
(B) Prolactin infusion increased new periglomerular neurons in the olfactory bulb two weeks (2W) and 4 weeks (4W) after BrdU injections.
(C) Prolactin infusion increased BrdU-labeled cells in the forebrain SVZ in both male and female animals. In non-ovariectomized females and in males, intracerebroventricular infusions of prolactin (PRL) and PRL-releasing peptide (PRP) stimulated SVZ proliferation.

DETAILED DESCRIPTION OF THE INVENTION

The present invention provides a method of increasing neural stem cell numbers by using prolactin. The method can be practiced in vivo to obtain more neural stem cells in situ, which can in turn produce more neurons or glial cells to compensate for lost or dysfunctional neural cells. The method can also be practiced in vitro to produce a large number of neural stem cells in culture. The cultured stem cells can be used, for example, for transplantation treatment of patients or animals suffering from or suspected of having neurodegenerative diseases or conditions.

Prior to describing the invention in further detail, the terms used in this application are defined as follows unless otherwise indicated.

Definitions

A "neural stem cell" is a stem cell in the neural cell lineage. A stem cell is a cell which is capable of reproducing itself. In other words, daughter cells which result from stem cell divisions include stem cells. The neural stem cells are capable of ultimately differentiating into all the cell types in the neural cell lineage, including neurons, astrocytes and oligodendrocytes (astrocytes and oligodendrocytes are collectively called glia or glial cells). Thus, the neural stem cells referred to herein are multipotent neural stem cells.

A "neurosphere" is a group of cells derived from a single neural stem cell as the result of clonal expansion. A "primary neurosphere" refers to the neurospheres generated by plating as primary cultures brain tissue which contains neural stem cells. The method for culturing neural stem cells to form neurospheres has been described in, for example, U.S. Pat. No. 5,750,376. A "secondary neurosphere" refers to the neurospheres generated by dissociating primary neurospheres and allowing the individual dissociated cells to form neurospheres again.

A polypeptide which shares "substantial sequence similarity" with a native factor is at least about 30% identical with the native factor at the amino acid level. The polypeptide is preferably at least about 40%, more preferably at least about 60%, yet more preferably at least about 70%, and most preferably at least about 80% identical with the native factor at the amino acid level.

The phrase "percent identity" or "% identity" of an analog or variant with a native factor refers to the percentage of amino acid sequence in the native factor which are also found in the analog or variant when the two sequences are aligned. Percent identity can be determined by any methods or algorithms established in the art, such as LALIGN or BLAST.

A polypeptide possesses a "biological activity" of a native factor if it is capable of binding to the receptor for the native factor or being recognized by a polyclonal antibody raised against the native factor. Preferably, the polypeptide is capable of specifically binding to the receptor for the native factor in a receptor binding assay.

A "functional agonist" of a native factor is a compound that binds to and activates the receptor of the native factor, although it does not necessarily share a substantial sequence similarity with the native factor.

A "prolactin" is a polypeptide which (1) shares substantial sequence similarity with a native mammalian prolactin, preferably the native human prolactin; and (2) possesses a biological activity of the native mammalian prolactin. The native human prolactin is a 199-amino acid polypeptide synthesized mainly in the pituitary gland. Thus, the term "prolactin" encompasses prolactin analogs which are the deletional, insertional, or substitutional mutants of the native prolactin. Furthermore, the term "prolactin" encompasses the prolactins from other species and the naturally occurring variants thereof.

In addition, a "prolactin" may also be a functional agonist of a native mammalian prolactin receptor. For example, the functional agonist may be an activating amino acid sequence disclosed in U.S. Pat. No. 6,333,031 for the prolactin receptor; a metal complexed receptor ligand with agonist activities for the prolactin receptor (U.S. Pat. No. 6,413,952); G120RhGH, which is an analog of human growth hormone but acts as a prolactin agonist (Mode et al., 1996); or a ligand for the prolactin receptor as described in U.S. Pat. Nos. 5,506,107 and 5,837,460.

An "EGF" means a native EGF or any EGF analog or variant that shares a substantial amino acid sequence similarity with a native EGF, as well as at least one biological activity with the native EGF, such as binding to the EGF receptor. Particularly included as an EGF is the native EGF of any species, TGFα, or recombinant modified EGF. Specific examples include, but are not limited to, the recombinant modified EGF having a deletion of the two C-terminal amino acids and a neutral amino acid substitution at position 51 (particularly EGF51gln51; U.S. Patent Application Publication No. 20020098178A1), the EGF mutein (EGF-$X_{16}$) in which the His residue at position 16 is replaced with a neutral or acidic amino acid (U.S. Pat. No. 6,191,106), the 52-amino acid deletion mutant of EGF which lacks the amino terminal residue of the native EGF (EGF-D), the EGF deletion mutant in which the N-terminal residue as well as the two C-terminal residues (Arg-Leu) are deleted (EGF-B), the EGF-D in which the Met residue at position 21 is oxidized (EGF-C), the EGF-B in which the Met residue at position 21 is oxidized (EGF-A), heparin-binding EGF-like growth factor (HB-EGF), betacellulin, amphiregulin, neuregulin, or a fusion protein comprising any of the above. Other useful EGF analogs or variants are described in U.S. Patent Application Publication No. 20020098178A1, and U.S. Pat. Nos. 6,191,106 and 5,547,935.

In addition, an "EGF" may also be a functional agonist of a native mammalian EGF receptor. For example, the functional agonist may be an activating amino acid sequence disclosed in U.S. Pat. No. 6,333,031 for the EGF receptor, or an antibody that has agonist activities for the EGF receptor (Fernandez-Pol, 1985 and U.S. Pat. No. 5,723,115).

A "PACAP" means a native PACAP or any PACAP analog or variant that shares a substantial amino acid sequence similarity with a native PACAP, as well as at least one biological activity with the native PACAP, such as binding to the PACAP receptor. Useful PACAP analogs and variants include, without being limited to, the 38 amino acid and the 27 amino acid variants of PACAP (PACAP38 and PACAP27, respectively), and the analogs and variants disclosed in, e.g., U.S. Pat. Nos. 5,128,242; 5,198,542; 5,208,320; 5,326,860; 5,623,050; 5,801,147 and 6,242,563.

In addition, a "PACAP" may also be a functional agonist of a native mammalian PACAP receptor. For example, the functional agonist may be maxadilan, a polypeptide that acts as a specific agonist of the PACAP type-1 receptor (Moro et al., 1997).

An "erythropoietin (EPO)" means a native EPO or any EPO analog or variant that shares a substantial amino acid sequence similarity with a native EPO, as well as at least one biological activity with the native EPO, such as binding to the EPO receptor. Erythropoietin analogs and variants are disclosed, for example, in U.S. Pat. Nos. 6,048,971 and 5,614,184.

In addition, an "EPO" may also be a functional agonist of a native mammalian EPO receptor. For example, the functional agonist may be EMP1 (EPO mimetic peptide 1, Johnson et al., 2000); one of the short peptide mimetics of EPO as described in Wrighton et al., 1996 and U.S. Pat. No. 5,773,569; any small molecular EPO mimetic as disclosed in Kaushansky, 2001; an antibody that activates the EPO receptor as described in U.S. Pat. No. 5,885,574, WO 96/40231, WO 97/48729, Fernandez-Pol, 1985 or U.S. Pat. No. 5,723,115; an activating amino acid sequence as disclosed in U.S. Pat. No. 6,333,031 for the EPO receptor; a metal complexed receptor ligand with agonist activities for the EPO receptor (U.S. Pat. No. 6,413,952), or a ligand for the EPO receptor as described in U.S. Pat. Nos. 5,506,107 and 5,837,460.

A "prolactin-inducing agent" is a substance that, when given to an animal, is capable of increasing the amount of prolactin in the animal. For example, prolactin releasing peptide stimulates the secretion of prolactin.

"Enhancing" the formation of a cell type means increasing the number of the cell type. Thus, a factor can be used to enhance neuron formation if the number of neurons in the presence of the factor is larger than the number of neurons absent the factor. The number of neurons in the absence of the factor may be zero or more.

A "neurodegenerative disease or condition" is a disease or medical condition associated with neuron loss or dysfunction. Examples of neurodegenerative diseases or conditions include neurodegenerative diseases, brain injuries or CNS dysfunctions. Neurodegenerative diseases include, for example, Alzheimer's disease, multiple sclerosis (MS), macular degeneration, glaucoma, diabetic retinopathy, peripheral neuropathy, Huntington's disease, amyotrophic lateral sclerosis, and Parkinson's disease. Brain injuries include, for example, stroke (e.g., hemorrhagic stroke, focal ischemic stroke or global ischemic stroke) and traumatic brain injuries (e.g. injuries caused by a brain surgery or physical accidents). CNS dysfunctions include, for example, depression, epilepsy, neurosis and psychosis.

"Treating or ameliorating" means the reduction or complete removal of the symptoms of a disease or medical condition.

A mammal "suspected of having a neurodegenerative disease or condition" is a mammal which is not officially diagnosed with the neurodegenerative disease or condition but shows a symptom of the neurodegenerative disease or condition, is susceptible to the neurodegenerative disease or condition due to family history or genetic predisposition, or has previously had the neurodegenerative disease or condition and is subject to the risk of recurrence.

"Transplanting" a composition into a mammal refers to introducing the composition into the body of the mammal by any method established in the art. The composition being introduced is the "transplant", and the mammal is the "recipient". The transplant and the recipient may be syngeneic, allogeneic or xenogeneic. Preferably, the transplantation is an autologous transplantation.

An "effective amount" is an amount of a therapeutic agent sufficient to achieve the intended purpose. For example, an effective amount of a prolactin to increase the number of neural stem cells is an amount sufficient, in vivo or in vitro, as the case may be, to result in an increase in neural stem cell number. An effective amount of a prolactin to treat or ameliorate a neurodegenerative disease or condition is an amount of the prolactin sufficient to reduce or remove the symptoms of the neurodegenerative disease or condition. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

Methods

In an attempt to assess the effects of pregnancy-associated hormonal/physiological changes on the brain, we discovered that the number of neural stem cells (NSCs) increases during pregnancy in a two-wave pattern. Thus, NSC numbers increased in a detectable manner at gestational day 7, reached a maximum of 40% increase at gestational day 14 and returned to baseline at birth. Surprisingly, a second increase occurred after birth, during the first post-natal week. The number of proliferating cells in the subventricular zone where neural stem cells are primarily located also increased during pregnancy in a two-wave pattern: doubled at gestational day 7, returned to baseline at gestational day 14, and followed by a second increase at birth (Example 1).

This two-wave pattern is similar to the pattern of prolactin levels in the same period of time. Prolactin concentrations are high during the first half of pregnancy, then decrease until the end of pregnancy when they rise again, presumably due to its role in lactation and maternal behaviors (reviewed in Freeman et al., 2000). Therefore, we investigated the effects of prolactin in neural stem cell number in vivo and in vitro (Examples 2 and 4). We found that prolactin is capable of inducing proliferation in the subventricular zone in vivo and increasing neural stem cell number in vitro.

In mammals, adult neural stem cells in the forebrain subventricular zone give rise to olfactory interneurons by forming neuronal progenitors that migrate along the rostral migratory stream to the olfactory bulb. Therefore, we also investigated whether pregnancy or prolactin-induced increase in neural stem cells results in olfactory interneuron formation. Indeed, the numbers of new olfactory interneurons in pregnant mice are significantly higher than those in their virgin counterparts. Moreover, after each of the two waves of neural stem cell increase, there is an increase in olfactory interneurons. Similarly, prolactin infusions led to significant increases in the number of new olfactory interneurons as well (Example 3).

The effect of prolactin and pregnancy on neurogenesis (about a 100% increase) is larger than that on stem cell proliferation (about 40-60%). Therefore, we determined whether prolaction is capable of promoting the differentiation of neural stem cells to neurons. To this end, neurospheres were cultured in the presence of EGF or EGF plus prolactin, and the numbers of neurons were counted (Example 5). The results indicate that neurospheres generated in the presence of both EGF and prolactin produced twice as many neurons as those generated in EGF alone. Accordingly, in addition to increasing proliferation of neural stem cells and new olfactory neuron production, prolactin also enhances neuron formation from neural stem cells.

The effects of prolactin on neural stem cells may be exerted directly or indirectly. In vivo, prolactin receptors were previously reported to reside in the choroid plexus of the forebrain lateral ventricles. Since the choroid plexus secretes growth factors that regulate neural stem cell proliferation, such as transforming growth factor alpha (TGFα), prolactin may stimulate the choroid plexus to secret TGFα, thereby inducing neural stem cells to proliferate. We discovered that prolactin receptors are also expressed in the dorsolateral corner of the SVZ, where neuronal progenitors depart for their migration along the rostral migratory stream to the olfactory bulb. Therefore, prolactin may also act on neural stem cells directly. Cultured neural stem cells were also found to have prolactin receptors.

Accordingly, the present invention provides a method of increasing neural stem cells numbers either in vivo or in vitro. When used to increase neural stem cell number in vivo, this method will result in a larger pool of neural stem cells in the brain. This larger pool of neural stem cells can subsequently generate more neural cells, particularly neurons or glial cells, than would a population of stem cells without prolactin. The neural cells, in turn, can compensate for lost or degenerate neural cells which are associated with neurodegenerative diseases and conditions, including nervous system injuries.

Prolactin can also be used to increase neural stem cell numbers in vitro. The resulting stem cells can be used to produce more neurons and/or glial cells in vitro, or used in transplantation procedures into humans or animals suffering from neurodegenerative diseases or conditions. It is preferable that neural stem cells produced according to the present invention, rather than neurons or glial cells, are transplanted. Once neural stem cells are transplanted, growth and/or differentiation factors can be administered in vivo to further increase the number of stem cells, or to selectively enhance neuron formation or glial cell formation. For example, we have found that erythropoietin induces selective production of neurons over glial cells. Cyclic AMP and factors which enhance the cAMP pathway, such as pituitary adenylate cyclase activating polypeptide (PACAP) and serotonin, are also good candidates for selectively promoting neuron production. On the other hand, bone morphogenetic protein (BMP) has been reported to inhibit neuron production and enhance glial production by adult SVZ cells (Lim et al., 2000). Factors that can increase neural stem cell number include, without being limited to, prolactin, epidermal growth factor (EGF), transforming growth factor alpha (TGFα), fibroblast growth factor (FGF), estrogen, growth hormone, insulin-like growth factor 1, and ciliary neurotrophic factor (CNTF).

Further provided by the present invention are methods of increasing neuron formation from neural stem cells in vitro or in vivo, as well as methods of enhancing new olfactory neuron production.

The increase in neural stem cells, neurons or olfactory interneurons is preferably at least about 10%, more preferably at least about 20%, even more preferably at least about 30%, yet more preferably at least about 40%, still more preferably at least about 50%, and further more preferably at least about 60%. Most preferably, the increase is at least about 80%.

The present invention also provides a method for treating or ameliorating a neurodegenerative disease or condition in an animal, particularly a mammal. This can be achieved, for example, by administering an effective amount of a prolactin to the brain of the mammal, or transplanting to the mammal neural stem cells, progenitor cells derived from neural stem cells, neurons and/or glial cells produced according to the present invention. Preferably, neural stem cells are transplanted. In addition to the transplantation, prolactin and/or additional factors can be further provided to the transplantation recipient, particularly concurrently with or after the transplantation.

One particularly interesting neurodegenerative condition is aging. We have found that the number of neural stem cells in the subventricular zone is significantly reduced in aged mice. Accordingly, it will be of particular interest to ameliorate problems associated with aging by increasing neural stem cell numbers with prolactin.

For example, the neural stem cell in the subventricular zone is the source of olfactory neurons, and olfactory dysfunction is a hallmark of forebrain neurodegenerative diseases, such as Alzheimer's, Parkinson's and Huntington's diseases. Disruption of neuronal migration to the olfactory bulb leads to deficits in olfactory discrimination, and doubling the new olfactory interneuons enhances new odor memory (Rochefort et al., 2002). Therefore, prolactin can be used to enhance olfactory discrimination or olfactory memory, as well as physiological functions that are associated with olfaction and olfactory discrimination, such as mating, offspring recognition and rearing. In addition, any other methods that result in an increase in neural stem cell number, particularly in the SVZ, will lead to elevated new olfactory neuron formation, thereby enhancing olfactory functions.

Another particularly important application of the present invention is the treatment and/or amelioration of brain injuries, such as stroke. As shown in Example 6, prolactin increased neurogenesis in the brain of animals that suffered from a chemically induced stroke. Furthermore, these animals also showed significant improvement in a motor-related symptom, demonstrating the effect of prolactin in the treatment of brain injuries. When prolactin and erythropoietin were combined in this treatment, the animals recovered completely behaviorally, and the cavities in the motor cortex, which resulted from the injury, were also completely or partially filled up by cells and tissues.

Therefore, prolactin can be used to treat or ameliorate neurodegenerative diseases or conditions, particularly brain injuries, and most particularly stroke. Preferably, prolactin, and/or any other methods of increasing neural stem cells, can be used in conjunction with an additional factor that enhances neurogenesis and/or glial formation. Prolactin and erythropoietin are a particularly preferred combination in the present invention. In addition, prolactin and EGF, as well as prolactin and PACAP, are also preferred embodiments.

Compositions

The present invention provides compositions that comprises a prolactin and at least one additional factor. The additional factor is capable of increasing neural stem cell number or enhancing neural stem cell differentiation to neurons or glial cells. The additional factor is preferably erythropoietin, EGF and/or PACAP.

Prolactin is a polypeptide hormone initially named for its activity to promote lactation. However, it is now known that prolactin has over 300 different biological activities not represented by its name (Freeman et al., 2000). Furthermore, although it is long believed that prolactin is synthesized in and secreted from specialized cells (the lactotrophs) of the anterior pituitary gland only, there is increasing evidence suggesting that other organs and tissues in the body can make prolactin as well.

The brain is among the organs reported to contain, and probably synthesize, prolactin. Prolactin immunoreactivity was first found in hypothalamic axon terminals, and subsequently found in the telencephalon in the cerebral cortex, hippocampus, amygdala, septum, caudate putamen, brain stem, cerebellum, spinal cord, choroid plexi, and the circumventricular organs. Known effects of prolactin on the central nervous system (CNS) include actions on maternal behavior, sexual behavior, grooming behavior, feeding behavior, sleep-wake cycle, the firing rate of hypothalamic neurons, and the metabolism of neurotransmitters and neuropeptides. Prolactin was also found to induce proliferation of astrocytes as well as astrocytic TGFα expression (DeVito et al., 1995). However, this is the first time prolactin is found to have an impact on neural stem cells.

In the human genome, a single gene encodes prolactin. The prolactin gene, found on chromosome 6, is 10 kb in size and contains 5 exons and 4 introns. Transcription of the prolactin gene is regulated by two independent promoter regions. The proximal 5 kb region directs pituitary-specific expression, while a more upstream promoter region is responsible for extrapituitary expression. The gene codes for a 227 amino acid prolactin prohormone, which is processed to the 199 amino acid mature human prolactin.

Although the major form of prolactin found in the pituitary gland has a molecular weight of 23 kDa, variants of prolactin have been characterized in many mammals, including humans. Prolactin variants can result from alternative splicing of the primary transcript, proteolytic cleavage and other post-translational modifications. A prolactin variant of 137 amino acids has been described in the anterior pituitary, which is likely to be a product of alternative splicing. A variety of proteolytic products of prolactin have been characterized, particularly the 14-, 16- and 22-kDa prolactin variants, all of which appear to be prolactin fragments truncated at the C-terminus. Other post-translational modification reported for prolactin include dimerization, polymerization, phosphorylation, glycosylation, sulfation and deamidation.

The prolactin useful in the present invention includes any prolactin analog, variant or prolactin-related protein which is capable of increasing neural stem cell number. A prolactin analog or variant is a polypeptide which contains at least about 30% of the amino acid sequence of the native human prolactin, and which possesses a biological activity of prolactin. Preferably, the biological activity of prolactin is the ability to bind prolactin receptors. Although several isoforms of the prolactin receptor have been isolated, for example the long, intermediate and short forms in rat, the isoforms share the same extracellular domain which binds prolactin. Therefore, any receptor isoform can be used to assay for prolactin binding activity. Specifically included as prolactins are the naturally occurring prolactin variants, prolactin-related protein, placental lactogens, S179D-human prolactin (Bernichtein et al., 2001), prolactins from various mammalian species, including but not limited to, human, other primates, rat, mouse, sheep, pig, and cattle, and the prolactin mutants described in U.S. Pat. Nos. 6,429,186 and 5,955,346.

Similarly, any additional compounds or factors that are useful in the present invention include their analogs and variants that share a substantial similarity and at least one biological activity with the native compounds or factors. For example, EGF can be used in conjunction with prolactin in the present invention. In addition to native EGF, an EGF analog or variant can also be used, which should share a substantial amino acid sequence similarity with the native EGF, as well as at least one biological activity with the native EGF, such as binding to the EGF receptor. Particularly included as an EGF is the native EGF of any species, TGFα, or recombinant modified EGF. Specific examples include, but are not limited to, the recombinant modified EGF having a deletion of the two C-terminal amino acids and a neutral amino acid substitution at position 51 (particularly EGF51gln51; U.S. Patent Application Publication No. 20020098178A1), the EGF mutein (EGF-$X_{16}$) in which the His residue at position 16 is replaced with a neutral or acidic amino acid (U.S. Pat. No. 6,191,106), the 52-amino acid deletion mutant of EGF which lacks the amino terminal residue of the native EGF (EGF-D), the EGF deletion mutant in which the N-terminal residue as well as the two C-terminal residues (Arg-Leu) are deleted (EGF-B), the EGF-D in which the Met residue at position 21 is oxidized (EGF-C), the EGF-B in which the Met residue at position 21 is oxidized (EGF-A), heparin-binding EGF-like growth factor (HB-EGF), betacellulin, amphiregulin, neuregulin, or a fusion protein comprising any of the above. Other useful EGF analogs or variants are described in U.S. Patent Application Publication No. 20020098178A1, and U.S. Pat. Nos. 6,191,106 and 5,547,935.

As another example, PACAP can also be used in conjunction with prolactin. Useful PACAP analogs and variants include, without being limited to, the 38 amino acid and the 27 amino acid variants of PACAP (PACAP38 and PACAP27, respectively), and the analogs and variants disclosed in, e.g., U.S. Pat. Nos. 5,128,242; 5,198,542; 5,208,320; 5,326,860; 5,623,050; 5,801,147 and 6,242,563.

Erythropoietin analogs and variants are disclosed, for example, in U.S. Pat. Nos. 6,048,971 and 5,614,184.

Further contemplated in the present invention are functional agonists of prolactin or additional factors useful in the present invention. These functional agonists bind to and activate the receptor of the native factor, although they do not necessarily share a substantial sequence similarity with the native factor. For example, maxadilan is a polypeptide that acts as a specific agonist of the PACAP type-1 receptor (Moro et al., 1997).

Functional agonists of EPO have been extensively studied. EMP1 (EPO mimetic peptide 1) is one of the EPO mimetics described in Johnson et al., 2000. Short peptide mimetics of EPO are described in, e.g., Wrighton et al., 1996 and U.S. Pat. No. 5,773,569. Small molecular EPO mimetics are disclosed in, e.g., Kaushansky, 2001. Antibodies that activate the EPO receptor are described in, e.g., U.S. Pat. No. 5,885,574; WO 96/40231 and WO 97/48729).

Antibodies that have agonist activities for the EGF receptor are described, e.g., in Fernandez-Pol, 1985 and U.S. Pat. No. 5,723,115. In addition, activating amino acid sequences are also disclosed in U.S. Pat. No. 6,333,031 for the EPO receptor, EGF receptor, prolactin receptor and many other cell surface receptors; metal complexed receptor ligands with agonist activities for the prolactin and EPO receptors can be found in U.S. Pat. No. 6,413,952. Other methods of identifying and preparing ligands for receptors, e.g., EPO and prolactin receptors, are described, for example, in U.S. Pat. Nos. 5,506,107 and 5,837,460.

It should be noted that the effective amount of each analog, variant or functional agonist may be different from that for the native factor or compound, and the effective amount in each case can be determined by a person of ordinary skill in the art according to the disclosure herein. Preferably, the native factors, or analogs and variants that share substantial sequence similarity with the native factors, are used in the present invention.

Pharmaceutical compositions are also provided, comprising a prolactin, an additional factor as described above, and a pharmaceutically acceptable excipient and/or carrier.

The pharmaceutical compositions can be delivered via any route known in the art, such as parenterally, intrathecally, intravascularly, intravenously, intramuscularly, transdermally, intradermally, subcutaneously, intranasally, topically, orally, rectally, vaginally, pulmonarily or intraperitoneally. Preferably, the composition is delivered into the central nervous system by injection or infusion. More preferably it is delivered into a ventricle of the brain, particularly the lateral ventricle. Alternatively, the composition is preferably delivered by systemic routes, such as subcutaneous administration. For example, we have discovered that prolactin, growth hormone, IGF-1, PACAP and EPO can be effectively delivered by subcutaneous administration to modulate the number of neural stem cells in the subventricular zone.

When the composition is not directly delivered into the brain, and factors in the composition do not readily cross the blood brain barrier, a blood brain barrier permeabilizer can be optionally included to facilitate entry into the brain. Blood brain barrier permeabilizers are known in the art and include, by way of example, bradykinin and the bradykinin agonists described in U.S. Pat. Nos. 5,686,416; 5,506,206 and 5,268,164 (such as $NH_2$-arginine-proline-hydroxyproxyproline-glycine-thienylalanine-serine-proline-4-Me-tyrosineψ($CH_2NH$)-arginine-COOH). Alternatively, the factors can be conjugated to the transferrin receptor antibodies as described in U.S. Pat. Nos. 6,329,508; 6,015,555; 5,833,988 or 5,527,527. The factors can also be delivered as a fusion protein comprising the factor and a ligand that is reactive with a brain capillary endothelial cell receptor, such as the transferrin receptor (see, e.g., U.S. Pat. No. 5,977,307).

The pharmaceutical compositions can be prepared by mixing the desired therapeutic agents with an appropriate vehicle suitable for the intended route of administration. In making the pharmaceutical compositions of this invention, the therapeutic agents are usually mixed with an excipient, diluted by an excipient or enclosed within such a carrier which can be in the form of a capsule, sachet, paper or other container. When the pharmaceutically acceptable excipient serves as a diluent, it can be a solid, semi-solid, or liquid material, which acts as a vehicle, carrier or medium for the therapeutic agent. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the therapeutic agents, soft and hard gelatin capsules, suppositories, sterile injectable solutions, and sterile packaged powders.

Some examples of suitable excipients include artificial cerebral spinal fluid, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the therapeutic agents after administration to the patient by employing procedures known in the art.

For preparing solid compositions such as tablets, the therapeutic agent is mixed with a pharmaceutical excipient to form a solid preformulation composition containing a homogeneous mixture of a compound of the present invention. When referring to these preformulation compositions as homogeneous, it is meant that the therapeutic agents are dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. The compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

Another formulation employed in the methods of the present invention employs transdermal delivery devices ("patches"). Such transdermal patches may be used to provide continuous or discontinuous infusion of the therapeutic agent of the present invention in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on demand delivery of pharmaceutical agents.

Other suitable formulations for use in the present invention can be found in *Remington's Pharmaceutical Sciences*.

The following examples are offered to illustrate this invention and are not to be construed in any way as limiting the scope of the present invention.

EXAMPLES

In the examples below, the following abbreviations have the following meanings. Abbreviations not defined have their generally accepted meanings.

| | |
|---|---|
| ° C. = | degree Celsius |
| hr = | hour |
| min = | minute |
| µM = | micromolar |
| mM = | millimolar |
| M = | molar |
| ml = | milliliter |
| µl = | microliter |
| mg = | milligram |
| µg = | microgram |
| FBS = | fetal bovine serum |
| PBS = | phosphate buffered saline |
| DMEM = | Dulbecco's modified Eagle's medium |
| α-MEM = | α-modified Eagle's medium |
| EGF = | epidermal growth factor |
| NSC = | neural stem cell |
| SVZ = | subventricular zone |
| PACAP = | pituitary adenylate cyclase activating polypeptide |
| cAMP = | cyclic AMP |
| BMP = | bone morphogenetic protein |
| CSF = | cerebral spinal fluid |

Materials and Methods

Neural Stem Cell Culture

The protocols for neural stem cell culture are described in detail in U.S. Pat. No. 5,750,376 or Shingo et al., 2001. Briefly, embryonic neural stem cells were prepared from E14 medial and lateral ganglionic eminences. Adult neural stem cells were prepared from the subventricular zone of adult mice. The tissue was cultured in basal medium containing 20 ng/ml EGF, or other growth factors as indicated in each case, to form neurospheres. The composition of the basal medium is as follows: DMEM/F12 (1:1); glucose (0.6%); glutamine (2 mM); sodium bicarbonate (3 mM); HEPES (5 mM); insulin (25 µg/ml); transferrin (100 µg/ml); progesterone (20 nM); putrescine (60 µM); and selenium chloride (30 nM).

Seven days later, the neurospheres (primary neurospheres) were passaged by mechanical dissociation and reseeded as single cells (passage 1). For secondary neurospheres, the single cells were then cultured for seven days to form secondary neurospheres.

Test Animals for the Stroke Study

Adult male Long-Evans rats (250-350 g) were obtained from Charles River Breeding Farms (Laval, Quebec, Canada) and were adapted to the colony for two weeks prior to any treatment. A week before surgery the rats were given a baseline testing on the forelimb inhibition test.

Focal Ischemic Injury and Infusion

The animals for the stroke study received unilateral devascularization of the sensorimotor cortex. Using Isoflurane anesthesia, the skin was incised and retracted and the overlying fascia were removed from the skull. A skull opening was made at the following coordinates, taking care not to damage the dura: AP+4.0 to −2.0; L 1.5 to 4 (the parasagittal ridge; Kolb et al., 1997). The dura was cut and retracted from the skull opening. A cotton swab soaked in sterile saline was gently rubbed across the exposed pia and the vessels were removed. A hole was then drilled in the contralateral hemisphere to provide an opening for the cannulae attached to the osmotic minipump at AP−0.5; L 1.5. An osmotic minipump was placed under the skin between the shoulder blades and a tube connected under the skin to the cannulae, which was attached to the skull with fast-drying cement. Once hemostasis had been achieved the scalp was sutured closed with 5-O sterile suture. The animals were given a single injection of Banamine (an analgesic) and returned to their home cage. Sham animals received only anesthesia, the bone opening, and the skin was incised and sutured.

Six days later the animals were assessed using the behavioral test and on the following day the animals were re-anesthetized and the minipump was replaced with a second one containing the appropriate solutions. Sham animals were only anesthetized. The animals were retested 7, 14, and 28 days later to yield behavioral measures on weeks 1,2,3,4, and 6.

Forelimb Inhibition Test

This test has been shown to constitute a sensitive measure of functional integrity of regions of anterior neocortex. In normal rats, swimming is accomplished by propulsion from the hind limbs. The forelimbs are normally inhibited from any stroking and are held immobile and together under the animal's neck. Inhibition of the forelimbs was assessed by filming animals while swimming. The animals were introduced into one end of an aquarium (30 w×90 l×43 h cm) filled to a depth of 25 cm with room temperature water (~25° C.) and filmed as they swim to a 9.5 cm square visible platform. This platform projects 2 cm above the surface of the water and is positioned at the opposite end of the aquarium. Scoring of inhibition was done by counting the number of strokes, if any, made by each forelimb in three swims along the length of the aquarium. A swim was deemed scorable only if the animal did not touch the sides of the aquarium during the swimming trial.

Brain Anatomical Analysis

At the conclusion of week 6 the animals were given an overdose of Euthanol and intracardially perfused with 0.9% saline and 4% paraformaldehyde in picric acid. The brains were cryoprotected and cut on a Vibratome at 40 microns. Five sets of sections were kept every 400 microns. Two sets were stained, one with Cresyl Violet and one with Doublecortin. The remaining sets were saved. The Cresyl Violet staining was performed on the slides whereas the Doublecortin was performed as an immunohistochemical procedure on free-floating sections. The Cresyl Violet staining allows assessment of lesion extent whereas the Doublecortin stains for a microtubule associated protein that is present in migrating neuronal progenitor cells.

Example 1 Neural Stem Cell Number Increases During Pregnancy

The numbers of neural stem cells in the forebrain of adult CD1 mice were determined in pregnant mice (6-8 weeks old) and age-matched virgin mice in order to investigate the effect of pregnancy. The entire subventricular zones of the forebrain (both hemispheres) of adult female mice were collected at various points during pregnancy, dissected, enzymatically dissociated and plated in defined culture medium in the presence of epidermal growth factor as described in U.S. Pat. No. 5,750,376. These cells were allowed to develop into primary neurospheres. Seven to ten days later, the numbers of neurospheres, each of which is clonally derived from a single stem cell, were counted.

In parallel experiments, numbers of proliferating cells in subventricular zones of mice during pregnancy were also assessed. The mice were labeled with bromodeoxyuridine (BrdU), and sections of subventricular zones were subjected to immunoassays with BrdU specific antibodies.

Figure 1:
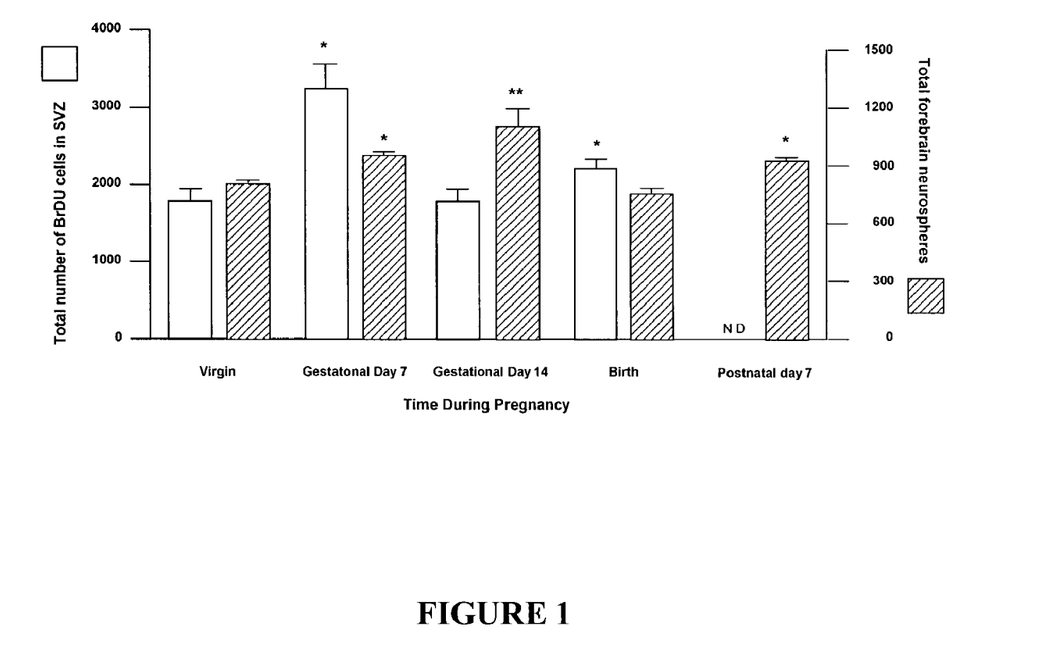
FIG. 1. Time course for SVZ proliferation and NSC numbers in pregnant female mice.
*significantly different from aged matched virgins, $p<0.05$.
**$p<0.01$.
N.D.: not determined.

The results of both measurements are shown in FIG. 1. In the forebrain of pregnant mice, NSC numbers increased transiently: first detectable at gestational day 7, reaching a maximum at gestational day 14 (40% increase) and returned to baseline at birth. Surprisingly, a second increase occurred after birth, during the first post-natal week. The number of BrdU immunoreactive cells also increased during pregnancy in a similar pattern which preceded the increases in NSC numbers: increased by 65% at gestational day 7, and returned to baseline at gestational day 14. At birth, a second increase (35%) in BrdU immunoreactive cells was observed. Therefore, both NSC number and proliferation in the subventricular zone increase in two waves during pregnancy and/or post-natal period.

Example 2 Prolactin Effect in vivo

The two-wave pattern of NSC number increase during pregnancy and/or post-natal period described in Example 1 is similar to the pattern of prolactin levels in the same period of time. Prolactin concentrations are high during the first half of pregnancy, then decrease until the end of pregnancy when they rise again, presumably due to its role in lactation and maternal behaviors (reviewed in Freeman et al., 2000). Although prolactin was first identified as a reproductive hormone, it has then become clear that its functions are highly diverse. The effects of prolactin on the central nervous system (CNS) include actions on maternal behavior, sexual behavior, grooming behavior, feeding behavior, sleep-wake cycle, the firing rate of hypothalamic neurons, and the metabolism of neurotransmitters and neuropeptides.

Figure 2:
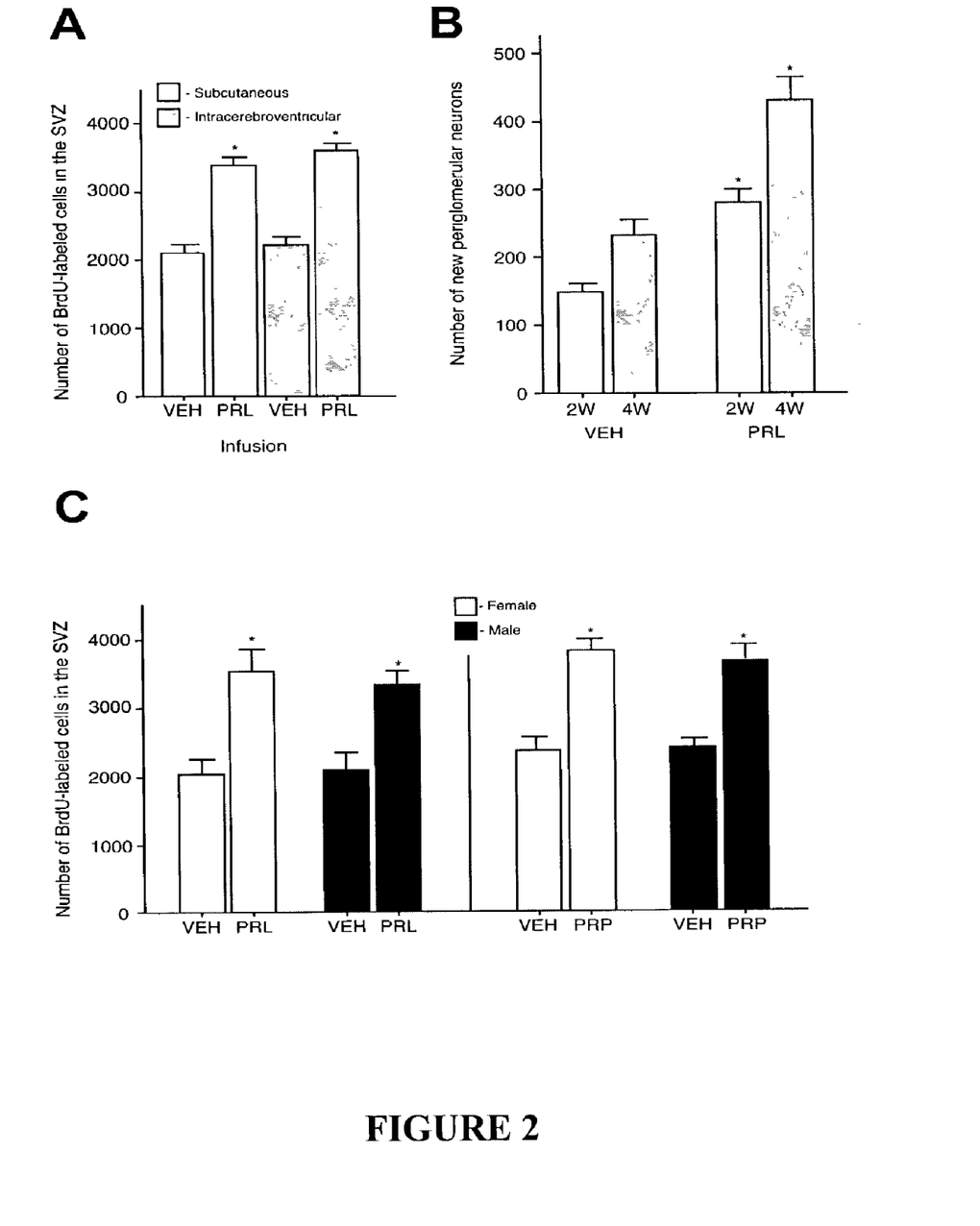

To determine if prolactin is capable of increasing NSC numbers, we infused prolactin into 6-8 week old ovariectomized mice either subcutaneously (SC, 8 μg/day for six days) or intracerebroventricularly (ICV, 0.8 μg/day for six days. BrdU was infused at the same time into the brain to assess proliferative activity in the brain. 6 days later, the number of BrdU immunoreactive cells were determined with BrdU specific antibodies. The results show that infusion of prolactin increased BrdU-labeled cells in the forebrain SVZ via both routes (an increase of 53% for SC and 61% for ICV; FIG. 2A). Therefore, prolactin can simulate cell proliferation in the subventricular zone, a main location of NSC in adult mice.

We further compared the response to prolactin in female and male animals, and the results are shown in FIG. 2C. Infusion of either prolactin (0.8 μg/day for six days) or prolactin releasing peptide (9 pg/day for six days) into the lateral ventricles increased proliferation in the forebrain SVZ in 6-8 week old male mice by 57% and 38%, respectively. These increases were comparable, albeit to a lesser extent, to those seen in age-matched non-ovariectomized females (74% and 56%, respectively). Therefore, prolactin can stimulate neural stem cell proliferation in both male and female animals.

Example 3 The Effects of Pregnancy and Prolactin on Olfactory Neurons

Since the SVZ neural stem cells are the source of ongoing neurogenesis in the olfactory bulb, we investigated if the effects of pregnancy and prolactin on neural stem cells are also reflected in olfactory neurogenesis. Virgin or age-matched pregnant 6-8 week old CD1 mice were injected with bromodeoxyuridine (BrdU) to label mitotic cells as in Example 1 on gestation day 7 or postpartum day 7. Four weeks after the BrdU injection, the number of BrdU labeled cells in various parts of the brain were counted. The pregnant mice that were injected on gestation day 7 had significantly more BrdU-labeled cells in both the granule and dopaminergic periglomerular cell layers of the olfactory bulb than their virgin counterparts. These results are consistent with the observation that pregnancy increases neural stem cells in the subventricular zone, which are known to form neuronal progenitor cells that migrate to the olfactory bulb.

Since the dopaminergic periglomerular layer of the olfactory bulb represents a homogeneous neuronal population, we then focused on this layer and counted the numbers of BrdU-labeled tyrosine hydroxylase-immunoreactive periglomerular neurons. Two or four weeks after BrdU injections, the pregnant mice labeled on both gestation day 7 and postpartum day 7 had 50-100% more new periglomerular neurons than the virgin controls. Therefore, each of the two waves of SVZ neural stem cell proliferation, in the gestation and postpartum stages, respectively, results in a doubling of new olfactory bulb interneuron formation.

We also determined whether neurogenesis in the olfactory bulb observed in pregnant mice was also stimulated by prolactin. Adult mice were infused with prolactin as described in Example 2, and the numbers of new olfactory interneurons were determined. The results show that new olfactory interneuron number doubled four weeks after prolactin infusion (FIG. 2B), indicating that prolactin infusions have the same effect on neurogenesis as pregnancy does, and prolactin is the maternal factor to mediate this physiological process.

Example 4 Prolactin Effect in vitro

Figure 3:
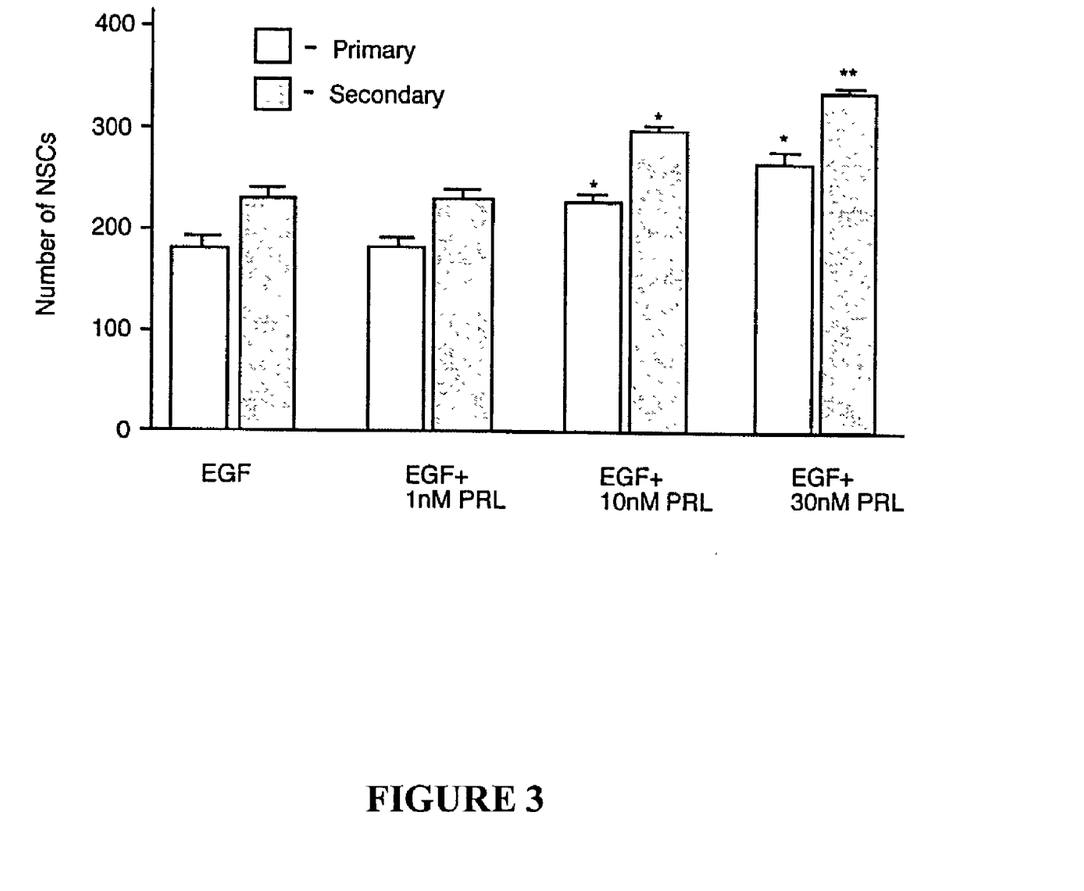
FIG. 3. Prolactin potentiated the effect of EGF to increase neurospheres. In the presence of EGF, prolactin (PRL) induced a dose-dependent increase in the proliferation of neural stem cells (NSCs), and in their self-renewal. *$p<0.05$. **$p<0.01$.

To determine the effect of prolactin on cultured neural stem cells, primary stem cell cultures were prepared as described in Materials and Methods. The cells were incubated for 7 days in the presence of EGF alone, or EGF plus prolactin, in addition to basal media. The number of the resulting neurospheres (primary neurospheres) were counted, and the neurospheres were dissociated to allow formation of secondary neurospheres. While prolactin alone did not significantly increase the number of neurospheres in vitro (data not shown), the results indicate that prolactin is capable of potentiating the effect of EGF to increase neurospheres (FIG. 3). Furthermore, the ability of primary neurospheres to generate secondary neurospheres was also increased by 25% in the presence of prolactin (FIG. 3). This is the first time prolactin is shown to act on neural stem cells.

Example 5 Prolactin Enhances Neuronal Differentiation

Figure 4:
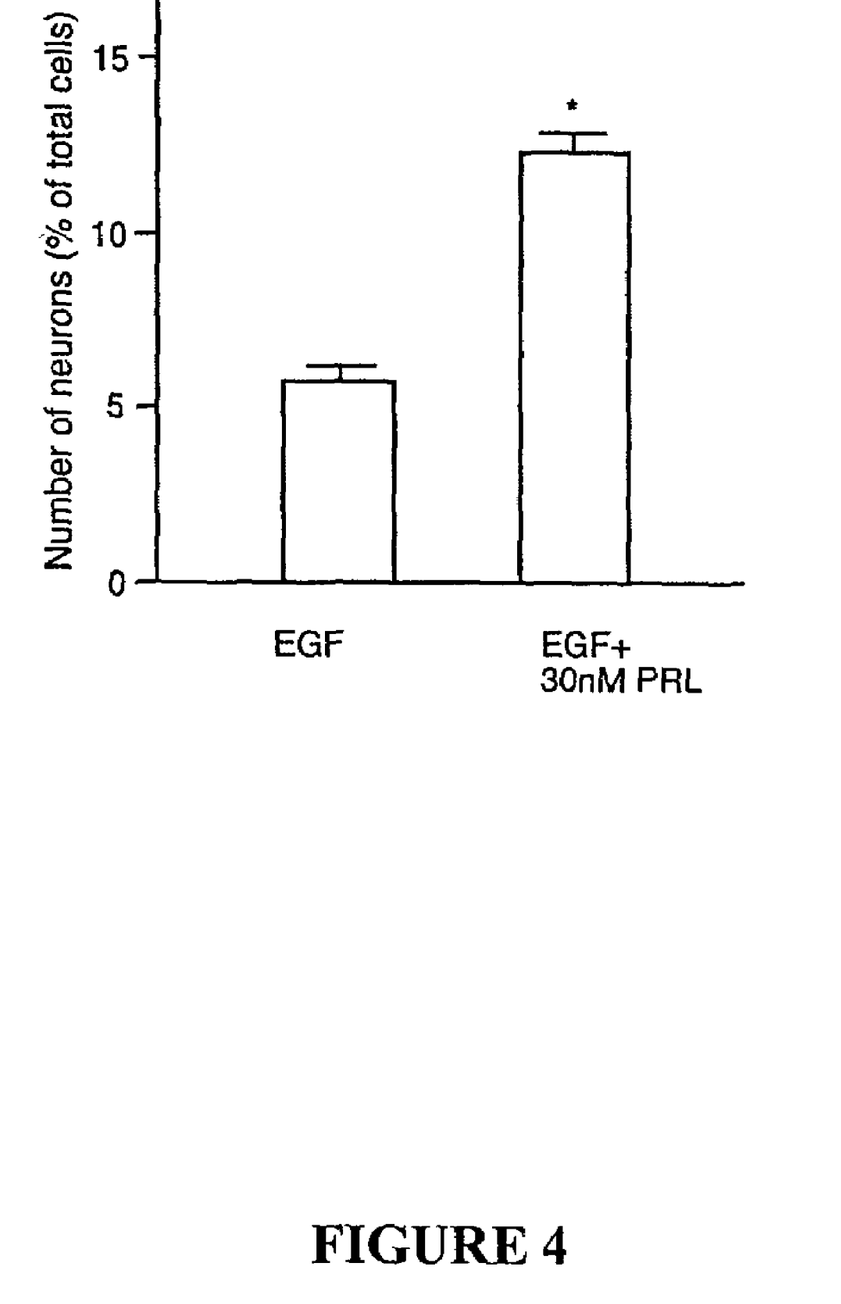
FIG. 4. Prolactin doubled the number of neurons produced by neural stem cells. Neurospheres grown in the presence of EGF alone or EGF plus 30 nM prolactin (PRL) were allowed to differentiate in basal media, and the percentage of neurons in neurospheres grown in EGF plus prolactin was twice as much as that in neurospheres grown in EGF alone. *$p<0.05$.

Neurospheres were cultured, as described in Example 4, in the presence of EGF alone or EGF plus 30 nM prolactin. Seven days later, the neurospheres were allowed to differentiate in basal media only, the numbers of neurons were determined by immunostaining for β-tubulin, counted, and expressed as percentages of total cells. As shown in FIG. 4, the percentage of neurons was twice as much when prolactin was included to grow neurospheres. Therefore, prolactin is capable of enhancing neuron formation from neural stem cells.

Example 6 The effect of Prolactin in a Stroke Model

In order to determine the effect of prolactin administration in animals that suffer a brain injury, focal ischemic injuries were introduced into the brains of rats as a model of stroke. As a result of the brain injury, the animals had lesions in the motor cortex and behaved abnormally in the forelimb inhibition test, which is a sensitive measure of functional integrity of regions of the anterior neocortex. The animals then received various test factors, and the effects of these factors on the forelimb inhibition test and brain anatomy were assessed. As controls, a sham control group received a sham brain injury and no test factors, and a vehicle control group received the brain injury as well as infusions of artificial cerebral spinal fluid (CSF). The treatments each test group received summarized below:

| Group | Brain Injury | First Infusion (days 1-7) | Second Infusion (days 8-14) |
|---|---|---|---|
| 1 | sham | none | none |
| 2 | yes | CSF | CSF |
| 3 | yes | prolactin | CSF |
| 4 | yes | prolactin | erythropoietin (EPO) |

The schedule and procedure of the brain injury, infusion, behavioral test and anatomical analysis are described in Materials and Methods.

Before the brain injury, all rats inhibited both forepaws in the forelimb inhibition test, which is expected from normal rats. After the injury, all ischemic groups (Groups 2-4) failed to inhibit the contralateral forepaw, but they continued to inhibit the ipsilateral forepaw. Upon infusion of the test factors, the two prolactin groups (Groups 3 and 4) showed greater forepaw inhibition. In fact, by the end of the last week (4 weeks after completion of the infusions), the prolactin plus EPO group (Group 4) was indistinguishable from the controls. Therefore, prolactin, and particularly the combination of prolactin and EPO, resulted in a recovery from a representative symptom of stroke.

Anatomically, the prolactin group showed a high degree of doublecortin staining in the brain, indicating that prolactin induced extensive neurogenesis. The rats in the prolactin plus EPO group had an expanded subventricular zone, indicating a significant cell increase in this area. In addition, many doublecortin positive cells appeared in the legioned area, white matter and the lateral ventricle. A stream of doublecortin positive cells could be observed between the subventricular zone and the lesioned area. Since doublecortin is a marker of migrating neuronal progenitor cells, these results indicate that neural stem cells gave rise to neuronal progenitor cells upon treatment, and the progenitor cells migrated to the lesioned area. The new growth in the lesioned area was so extensive that the cavities created by the ischemic injury were completely or partially filled up in a majority of the rats in this group. These anatomical results thus strongly support the behavioral study that prolactin, or the combination of prolactin and EPO, can be used to treat brain injuries such as stroke.

We claim:

1. A method of increasing neural stem cell number in a mammal, comprising selecting a mammal with a neurodegenerative disease or condition and systemically administering to said mammal an effective amount of a prolactin under conditions which result in an increase in the number of neural stem cells in the mammal.

2. The method of claim 1, wherein the prolactin is administered subcutaneously, intravenously, intravascularly, intramuscularly, or by inhalation.

3. The method of claim 1, wherein the mammal is an adult mammal.

4. The method of claim 1, further comprising providing to the mammal an additional factor selected from the group consisting of erythropoietin, cyclic AMP, pituitary adenylate cyclase activating polypeptide (PACAP), serotonin, bone morphogenetic protein (BMP), epidermal growth factor (EGF), transforming growth factor alpha (TGFα), fibroblast growth factor (FGF), estrogen, growth hormone, insulin-like growth factor 1, and ciliary neurotrophic factor (CNTF).

5. The method of claim 1, wherein the disease or condition is a brain injury.

6. The method of claim 5, wherein the brain injury is a stroke.

7. The method of claim 5, wherein the brain injury is associated with brain surgery.

8. The method of claim 1, wherein the disease or condition is selected from the group consisting of Alzheimer's disease, multiple sclerosis, Huntington's disease, amyotrophic lateral sclerosis, and Parkinson's disease.

9. A method of enhancing neuron formation in a mammal, comprising selecting a mammal with a neurodegenerative disease or condition and systemically administering a prolactin to the mammal under conditions that result in enhanced neuron formation from neural stem cells in the mammal.

10. The method of claim 9, wherein the prolactin is administered subcutaneously, intravenously, intravascularly, intramuscularly, or by inhalation.

11. The method of claim 9, wherein the mammal is an adult mammal.

12. The method of claim 9, further comprising providing to the mammal an additional factor selected from the group consisting of erythropoietin, cyclic AMP, pituitary adenylate cyclase activating polypeptide (PACAP), serotonin, bone morphogenetic protein (BMP), epidermal growth factor (EGF), transforming growth factor alpha (TGFα), fibroblast growth factor (FGF), estrogen, growth hormone, insulin-like growth factor 1, and ciliary neurotrophic factor (CNTF).

13. The method of claim 9, wherein the disease or condition is a brain injury.

14. The method of claim 13, wherein the brain injury is a stroke.

15. The method of claim 13, wherein the brain injury is associated with brain surgery.

16. The method of claim 9, wherein the disease or condition is selected from the group consisting of Alzheimer's disease, multiple sclerosis, Huntington's disease, amyotrophic lateral sclerosis, and Parkinson's disease.

17. A method of increasing new neuron formation in the olfactory bulb of a mammal, comprising selecting a mammal with a neurodegenerative disease or condition and systemically administering an effective amount of a prolactin to the mammal, wherein the amount is sufficient to increase new neuron formation in the olfactory bulb of the mammal.

18. The method of claim 17, wherein the prolactin is administered subcutaneously, intravenously, intravascularly, intramuscularly, or by inhalation.

19. The method of claim 17, wherein the mammal is an adult mammal.

20. The method of claim 17, further comprising providing to the mammal an additional factor selected from the group consisting of erythropoietin, cyclic AMP, pituitary adenylate cyclase activating polypeptide (PACAP), serotonin, bone morphogenetic protein (BMP), epidermal growth factor (EGF), transforming growth factor alpha (TGFα), fibroblast growth factor (FGF), estrogen, growth hormone, insulin-like growth factor 1, and ciliary neurotrophic factor (CNTF).

21. The method of claim 17, wherein the disease or condition is a brain injury.

22. The method of claim 21, wherein the brain injury is a stroke.

23. The method of claim 21, wherein the brain injury is associated with brain surgery.

24. The method of claim 17, wherein the disease or condition is selected from the group consisting of Alzheimer's disease, multiple sclerosis, Huntington's disease, amyotrophic lateral sclerosis, and Parkinson's disease.

* * * * *